(12) United States Patent
Pacheco et al.

(10) Patent No.: US 9,993,614 B2
(45) Date of Patent: Jun. 12, 2018

(54) COMPONENTS FOR MULTIPLE AXIS CONTROL OF A CATHETER IN A CATHETER POSITIONING SYSTEM

(71) Applicant: Catheter Precision, Inc., Ledgewood, NJ (US)

(72) Inventors: Robert Pacheco, Bayside, NY (US); Steve Foley, Kerrville, TX (US); David Jenkins, Budd Lake, NJ (US)

(73) Assignee: CATHETER PRECISION, INC., Ledgewood, NJ (US)

( * ) Notice: Subject to any disclaimer, the term of this patent is extended or adjusted under 35 U.S.C. 154(b) by 961 days.

(21) Appl. No.: 14/468,416

(22) Filed: Aug. 26, 2014

(65) Prior Publication Data

US 2015/0065952 A1 Mar. 5, 2015

Related U.S. Application Data

(60) Provisional application No. 61/870,310, filed on Aug. 27, 2013, provisional application No. 61/874,427, filed on Sep. 6, 2013.

(51) Int. Cl.
*A61M 25/01* (2006.01)
*A61B 34/30* (2016.01)

(52) U.S. Cl.
CPC ......... *A61M 25/0113* (2013.01); *A61B 34/30* (2016.02); *A61B 2034/301* (2016.02)

(58) Field of Classification Search
CPC .............................................. A61M 25/0113
(Continued)

(56) References Cited

U.S. PATENT DOCUMENTS

| 4,549,538 A | 10/1985 | Schadrack, III et al. |
| 4,721,123 A | 1/1988 | Cosentino et al. |

(Continued)

FOREIGN PATENT DOCUMENTS

| JP | 2007527296 A | 9/2007 |
| WO | 2005087128 A | 9/2005 |

(Continued)

OTHER PUBLICATIONS

WIPO, International Preliminary Report on Patentability; PCT/US2006/027024; dated Jan. 16, 2008; 8pgs.

(Continued)

*Primary Examiner* — David S Luo
(74) *Attorney, Agent, or Firm* — The Marbury Law Group, PLLC

(57) ABSTRACT

Various embodiments provide a catheter positioning device with components for controlling actuators of the catheter in multiple axes. A catheter may be attached to a sled member by a modular plate with one or more actuator interfaces that may couple with the actuators of a catheter handle. One or more motors or drives in the sled member may move the actuator interfaces of the modular plate to control one or more actuators on the catheter in different axes. In various embodiments the sled member may have a clam shell design in which two or more sides of the sled member close around the catheter handle. In further embodiments, the sled member may include adjustable faces that can fit different types of modular plates and thereby control actuators on different types of the catheter.

19 Claims, 40 Drawing Sheets

(58) Field of Classification Search
USPC .................. 318/568.11, 568.1, 567, 560
See application file for complete search history.

(56) References Cited

U.S. PATENT DOCUMENTS

| | | | |
|---|---|---|---|
| 5,226,892 A | 7/1993 | Boswell | |
| 5,644,551 A | 7/1997 | Carmichael et al. | |
| 5,649,956 A | 7/1997 | Jensen et al. | |
| 5,682,890 A | 11/1997 | Kormos et al. | |
| 5,810,880 A | 9/1998 | Jensen et al. | |
| 5,814,038 A | 9/1998 | Jensen et al. | |
| 5,855,583 A | 1/1999 | Wang et al. | |
| 6,007,550 A | 12/1999 | Wang et al. | |
| 6,063,095 A | 5/2000 | Wang et al. | |
| 6,080,181 A | 6/2000 | Jensen et al. | |
| 6,096,004 A | 8/2000 | Meglan et al. | |
| 6,132,368 A | 10/2000 | Cooper | |
| 6,171,234 B1 | 1/2001 | White et al. | |
| 6,171,277 B1 | 1/2001 | Ponzi | |
| 6,200,315 B1 | 3/2001 | Gaiser et al. | |
| 6,319,227 B1* | 11/2001 | Mansouri-Ruiz | A61B 8/12 600/466 |
| 6,346,072 B1 | 2/2002 | Cooper | |
| 6,396,232 B2 | 5/2002 | Haanpaa et al. | |
| 6,398,755 B1 | 6/2002 | Belef et al. | |
| 6,413,264 B1 | 7/2002 | Jensen et al. | |
| 6,445,984 B1 | 9/2002 | Kellogg | |
| 6,461,372 B1 | 10/2002 | Jensen et al. | |
| 6,485,482 B1* | 11/2002 | Belef | A61B 8/12 604/164.08 |
| 6,527,782 B2 | 3/2003 | Hogg et al. | |
| 6,620,174 B2 | 9/2003 | Jensen et al. | |
| 6,726,675 B1 | 4/2004 | Beyar | |
| 6,788,999 B2 | 9/2004 | Green | |
| 6,850,817 B1 | 2/2005 | Green | |
| 6,963,792 B1 | 11/2005 | Green | |
| 6,974,465 B2 | 12/2005 | Belef et al. | |
| 6,999,852 B2 | 2/2006 | Green | |
| 7,006,895 B2 | 2/2006 | Green | |
| 7,090,683 B2 | 8/2006 | Brock et al. | |
| 7,118,582 B1 | 10/2006 | Wang et al. | |
| 7,169,141 B2 | 1/2007 | Brock et al. | |
| 7,204,844 B2 | 4/2007 | Jensen et al. | |
| 7,214,230 B2 | 5/2007 | Brock et al. | |
| 7,276,044 B2 | 10/2007 | Ferry et al. | |
| 7,314,230 B2 | 1/2008 | Kumagai et al. | |
| 7,331,967 B2 | 2/2008 | Lee et al. | |
| 7,357,774 B2 | 4/2008 | Cooper | |
| 7,371,210 B2 | 5/2008 | Brock et al. | |
| 7,377,906 B2 | 5/2008 | Selkee | |
| 7,537,570 B2 | 5/2009 | Kastelein | |
| 7,630,752 B2 | 12/2009 | Viswanathan | |
| 7,648,513 B2 | 1/2010 | Green et al. | |
| 7,758,564 B2 | 7/2010 | Long et al. | |
| 8,046,049 B2 | 10/2011 | Govari et al. | |
| 8,672,880 B2 | 3/2014 | Cohen et al. | |
| 2001/0053879 A1 | 12/2001 | Mills et al. | |
| 2002/0042620 A1 | 4/2002 | Julian et al. | |
| 2002/0072704 A1 | 6/2002 | Mansouri-Ruiz | |
| 2002/0120254 A1 | 8/2002 | Julian et al. | |
| 2002/0177789 A1 | 11/2002 | Ferry et al. | |
| 2002/0183723 A1 | 12/2002 | Belef et al. | |
| 2004/0077942 A1 | 4/2004 | Hall et al. | |
| 2004/0254566 A1 | 12/2004 | Plicchi et al. | |
| 2005/0038412 A1 | 2/2005 | Rabiner et al. | |
| 2005/0065435 A1 | 3/2005 | Rauch et al. | |
| 2005/0113719 A1 | 5/2005 | Saadat | |
| 2005/0203382 A1 | 9/2005 | Govari et al. | |
| 2005/0209614 A1 | 9/2005 | Fenter et al. | |
| 2005/0222554 A1 | 10/2005 | Wallace et al. | |
| 2005/0228440 A1 | 10/2005 | Brock et al. | |
| 2005/0277874 A1 | 12/2005 | Selkee | |
| 2005/0283140 A1 | 12/2005 | Jensen et al. | |
| 2006/0009735 A1 | 1/2006 | Viswanathan et al. | |
| 2006/0041181 A1 | 2/2006 | Viswanathan et al. | |
| 2006/0084911 A1 | 4/2006 | Belef et al. | |
| 2006/0084945 A1 | 4/2006 | Moll et al. | |
| 2006/0095022 A1 | 5/2006 | Moll et al. | |
| 2006/0161136 A1 | 7/2006 | Anderson et al. | |
| 2006/0161137 A1 | 7/2006 | Orban et al. | |
| 2006/0161138 A1 | 7/2006 | Orban et al. | |
| 2006/0167441 A1 | 7/2006 | Wang et al. | |
| 2006/0178559 A1 | 8/2006 | Kumar et al. | |
| 2006/0229587 A1 | 10/2006 | Beyar | |
| 2006/0235436 A1 | 10/2006 | Anderson et al. | |
| 2006/0270915 A1 | 11/2006 | Ritter et al. | |
| 2006/0293643 A1 | 12/2006 | Wallace et al. | |
| 2007/0012135 A1 | 1/2007 | Tierney et al. | |
| 2007/0016174 A1 | 1/2007 | Cohen et al. | |
| 2007/0019330 A1 | 1/2007 | Wolfersberger | |
| 2007/0021776 A1 | 1/2007 | Jensen et al. | |
| 2007/0043338 A1 | 2/2007 | Moll et al. | |
| 2007/0043455 A1 | 2/2007 | Viswanathan et al. | |
| 2007/0149946 A1 | 6/2007 | Viswanathan et al. | |
| 2007/0233044 A1 | 10/2007 | Wallace et al. | |
| 2007/0239172 A1 | 10/2007 | Lee et al. | |
| 2007/0250073 A1 | 10/2007 | Brock et al. | |
| 2007/0250074 A1 | 10/2007 | Brock et al. | |
| 2007/0260115 A1 | 11/2007 | Brock et al. | |
| 2007/0276423 A1 | 11/2007 | Green | |
| 2007/0283263 A1 | 12/2007 | Zawde et al. | |
| 2007/0299479 A1 | 12/2007 | Saksena | |
| 2008/0009791 A1 | 1/2008 | Cohen et al. | |
| 2008/0039869 A1 | 2/2008 | Mills et al. | |
| 2008/0045892 A1 | 2/2008 | Ferry et al. | |
| 2008/0059598 A1 | 3/2008 | Garibaldi et al. | |
| 2008/0119824 A1 | 5/2008 | Weitzner et al. | |
| 2008/0119872 A1 | 5/2008 | Brock et al. | |
| 2008/0125793 A1 | 5/2008 | Brock et al. | |
| 2008/0125794 A1 | 5/2008 | Brock et al. | |
| 2008/0140087 A1 | 6/2008 | Barbagli | |
| 2008/0147091 A1 | 6/2008 | Cooper | |
| 2008/0183136 A1 | 7/2008 | Lenker et al. | |
| 2008/0215065 A1 | 9/2008 | Wang et al. | |
| 2008/0245946 A1 | 10/2008 | Yu | |
| 2008/0249536 A1 | 10/2008 | Stahler et al. | |
| 2008/0300592 A1 | 12/2008 | Weitzner et al. | |
| 2009/0012533 A1 | 1/2009 | Barbagli et al. | |
| 2009/0082722 A1 | 3/2009 | Munger et al. | |
| 2009/0105639 A1 | 4/2009 | Weitzner et al. | |
| 2009/0105645 A1 | 4/2009 | Kidd et al. | |
| 2009/0248043 A1 | 10/2009 | Tierney et al. | |
| 2010/0010475 A1 | 1/2010 | Teirstein et al. | |
| 2010/0256558 A1 | 10/2010 | Olson et al. | |
| 2011/0077590 A1 | 3/2011 | Plicchi et al. | |
| 2012/0182134 A1 | 7/2012 | Doyle | |
| 2012/0184955 A1 | 7/2012 | Pivotto et al. | |
| 2012/0197182 A1 | 8/2012 | Millman et al. | |
| 2013/0138118 A1 | 5/2013 | Doyle | |

FOREIGN PATENT DOCUMENTS

| | | |
|---|---|---|
| WO | 2007008967 A2 | 1/2007 |
| WO | 2009092059 A2 | 7/2009 |

OTHER PUBLICATIONS

State Intellectual Property Office of the People's Republic of China, First Office Action, dated Oct. 30, 2009, Chinese Patent Application 200680025512.7, "Remotely Controlled Catheter Insertion System," with English translation, (24 pgs. total).

Chinese Application 200680025512.7, State Intellectual Property Office of the People's Republic of China, Office Action dated Feb. 13, 2012.

Chinese Application 200980102420.8, State Intellectual Property Office of the People's Republic of China, Office Action dated Feb. 16, 2012.

International Preliminary Report on Patentability, Intl Application PCT/US2009/031357. International Bureau of WIPO, dated Jul. 29, 2010.

(56) References Cited

OTHER PUBLICATIONS

International Search Report and Written Opinion, Intl Application PCT/U52009/031357. International Search Authority, U.S. Patent and Trademark Office (ISA/US), Mar. 19, 2009.
U.S. Appl. 13/051,736, Final Office Action dated Nov. 5, 2012.
Hein et al., "Robot Supported insertion of Catheters for Hyperthermia and Branch Therapy," Computer Assisted Radiology and Surgery, 1998, pp. 660-663.
Macoviak, "Catheter System for Surgical Access and Circulatory Support of the Heart," USPTO, Official Gazette, vol. 1278, Jan. 6, 2004.
U.S. Appl. 13/051,736, Non-Final Office Action dated Jul. 17, 2012.
U.S. Appl. No. 12/903,397, Non-Final Office Action dated Nov. 19, 2012.
Canadian Application 2,646,846, Office Action dated Sep. 19, 2012.
Extended European Search Report of Apr. 17, 2013; European Application No. 09702983.9.
Japanese Patent Application No. 2010-543298; Office Action dated Mar. 19, 2013.
U.S. Appl. No. 13/461,463, Final Office Action dated Jun. 27, 2014.
U.S. Appl. No. 13/461,463, Non-Final Office Action dated Oct. 31, 2014.
U.S. Appl. No. 12/515,005, Non-Final Office Action dated Apr. 11, 2013.
U.S. Appl. No. 13/078,663, Non-Final Office Action dated Aug. 14, 2014.

\* cited by examiner

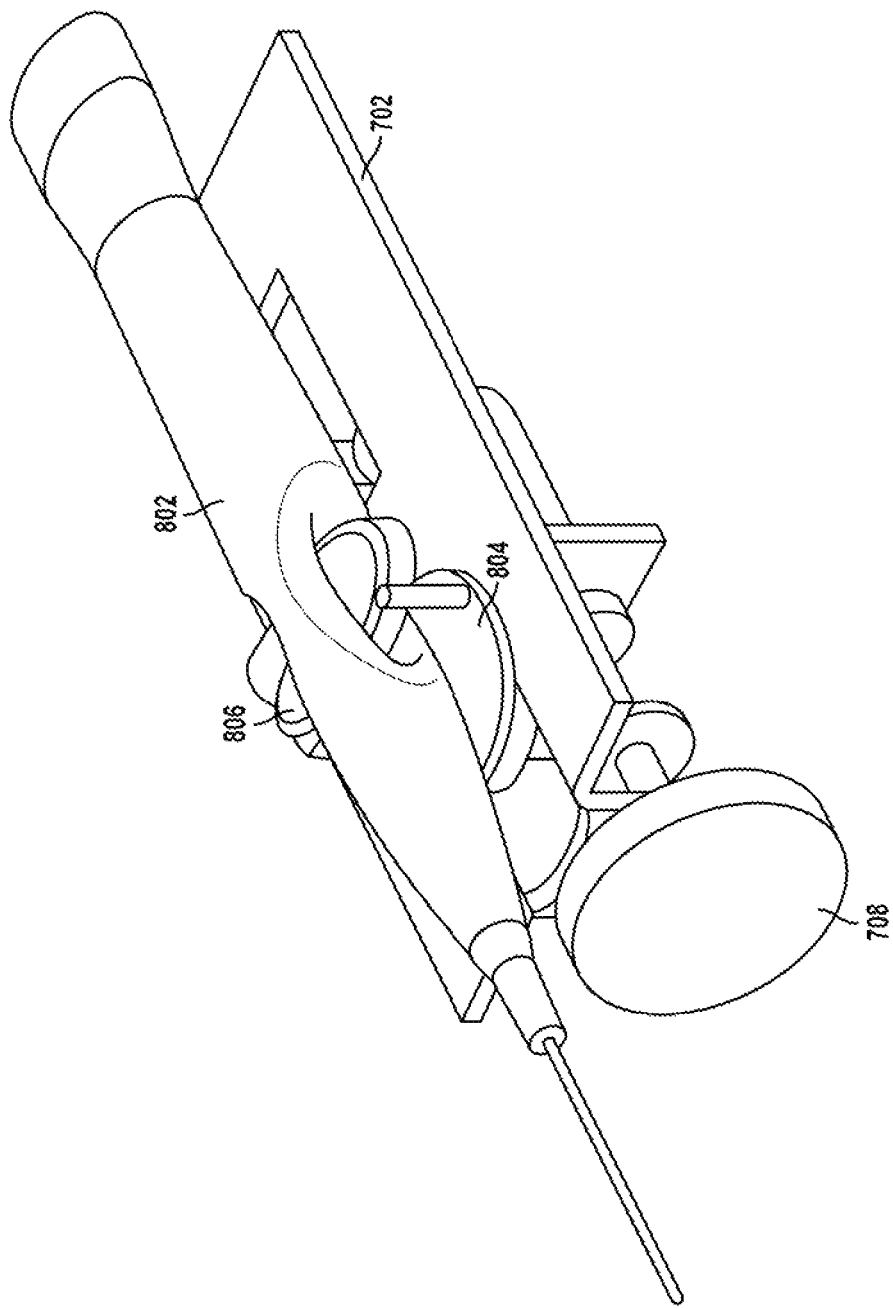

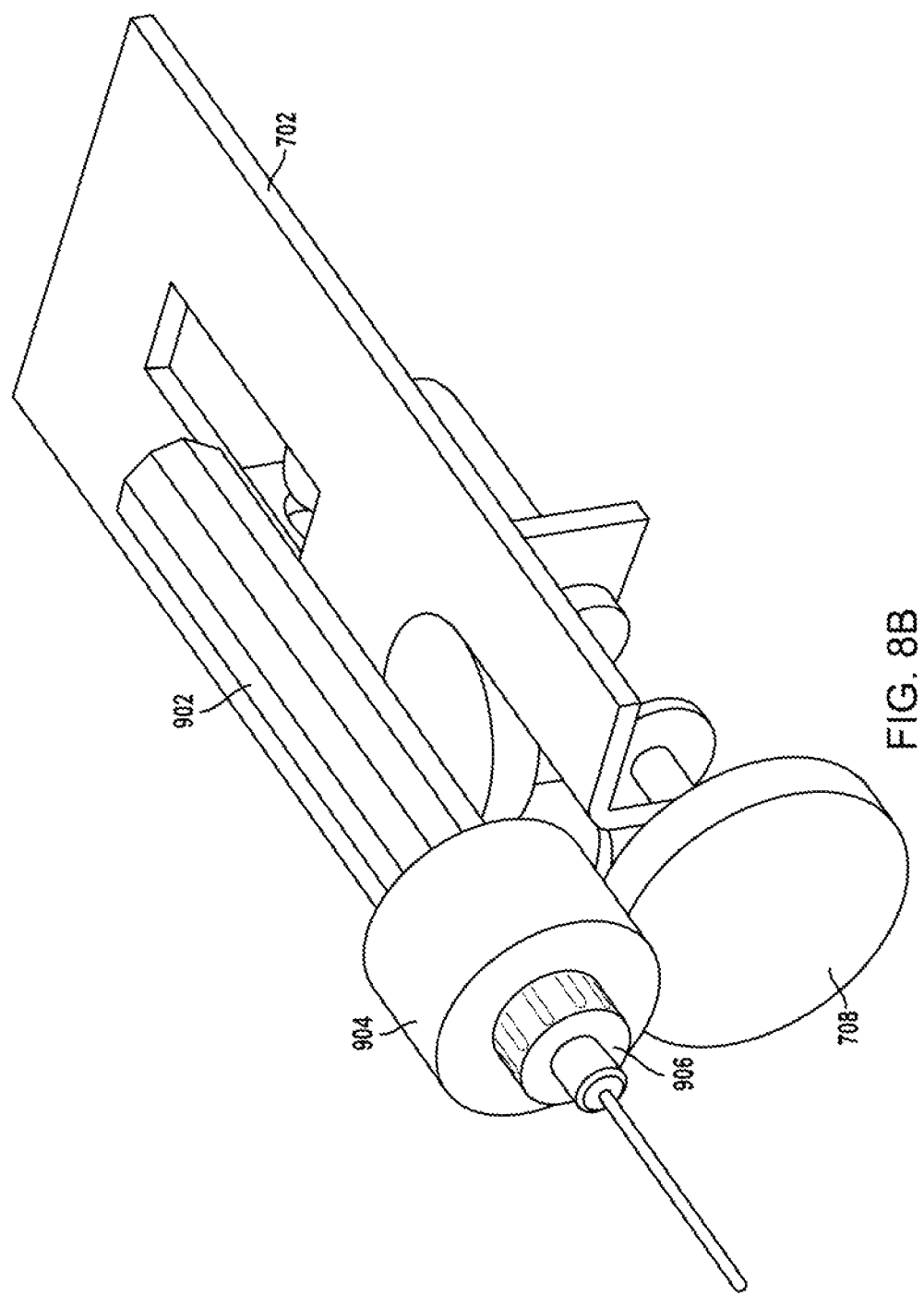

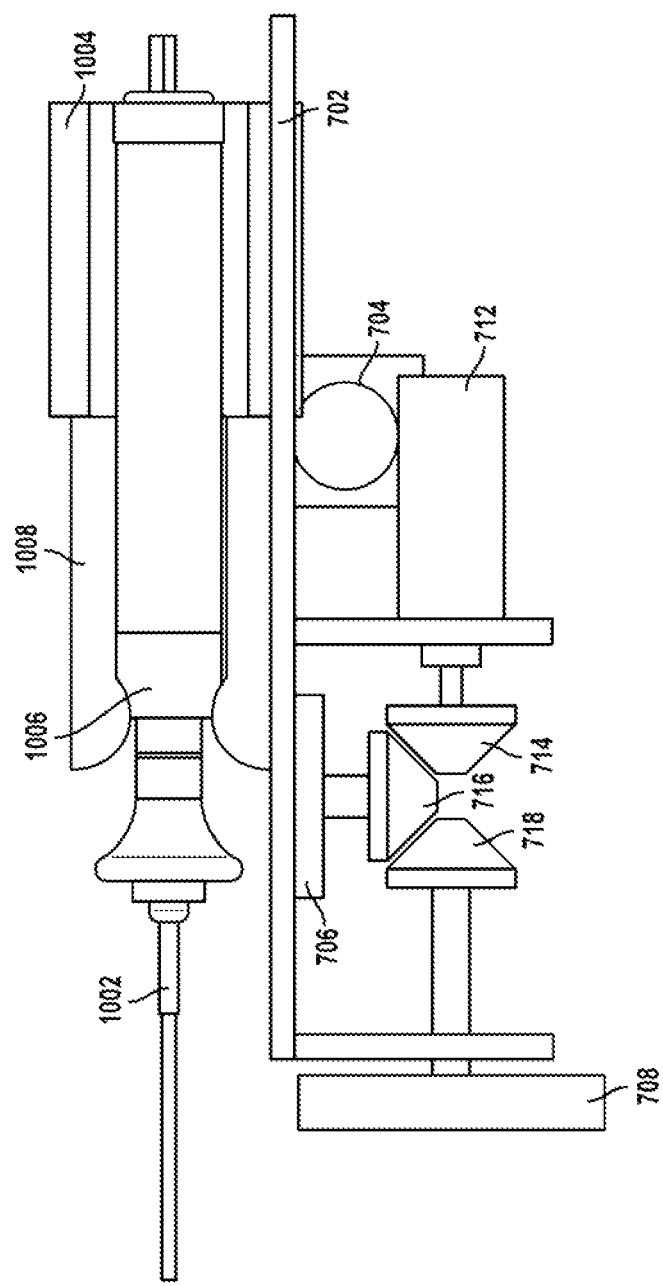

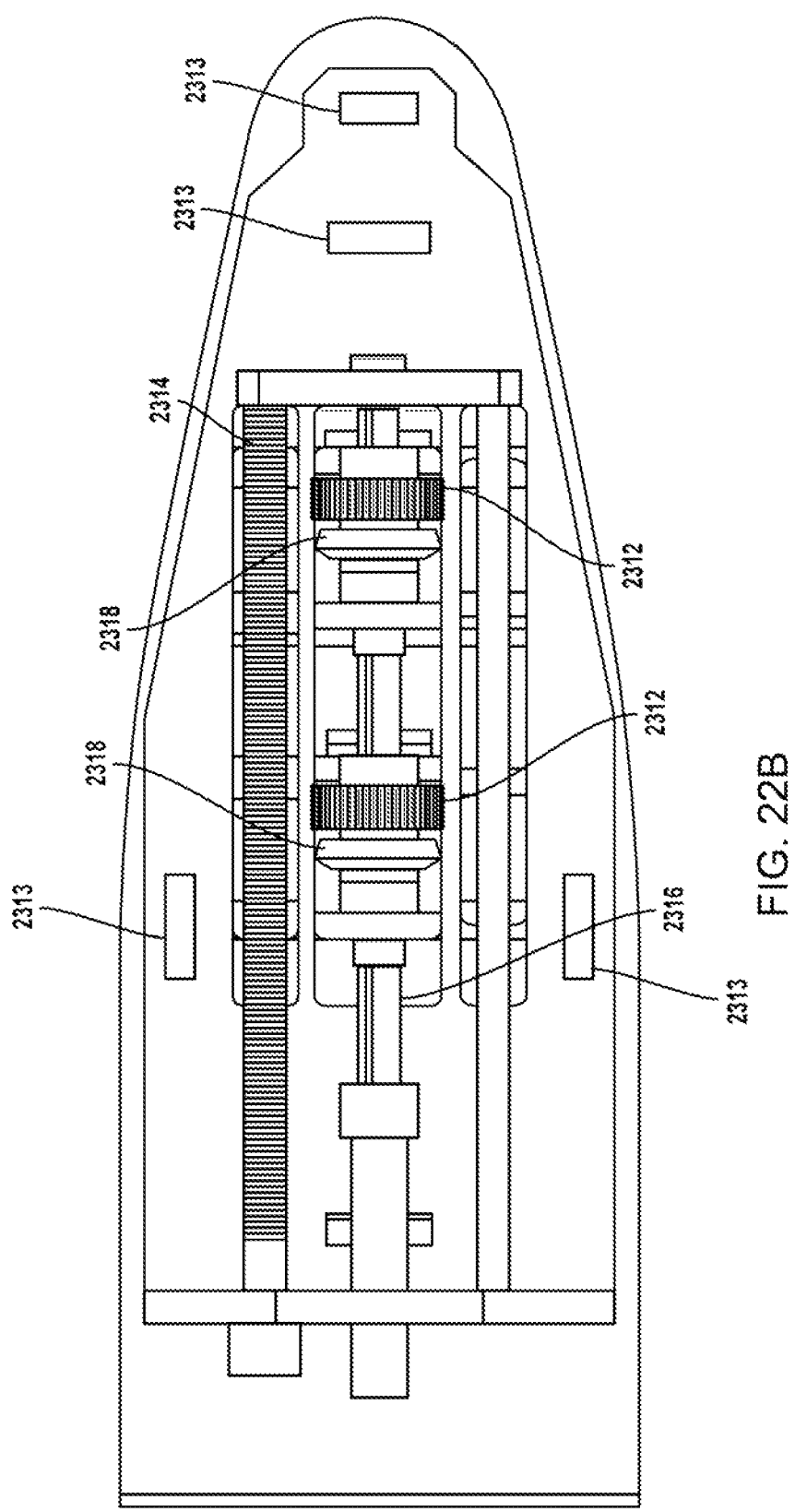

COMPONENTS FOR MULTIPLE AXIS CONTROL OF A CATHETER IN A CATHETER POSITIONING SYSTEM

CROSS REFERENCE TO RELATED APPLICATIONS

This application claims the benefit of priority to U.S. Provisional Patent Application No. 61/870,310, entitled "COMPONENTS AND METHODS FOR MULTIPLE AXIS CONTROL OF A CATHETER IN A CATHETER POSITIONING SYSTEM," filed Aug. 27, 2013, and to U.S. Provisional Patent Application No. 61/874,427, also entitled "COMPONENTS AND METHODS FOR MULTIPLE AXIS CONTROL OF A CATHETER IN A CATHETER POSITIONING SYSTEM," filed Sep. 6, 2013, the entire contents of both of which are incorporated herein by reference.

BACKGROUND

Many procedures involving catheter insertion, such as invasive electrophysiology procedures, rely on fluoroscopy or other radioactive imaging techniques to help navigate and position the catheter within a patient's body at a particular site, such as in the heart or inside a blood vessel in the circulatory system. High dosages of radiation can have long term adverse health effects. A patient may be directly exposed only once or twice to radiation during such procedures and avoid such adverse effects. However, physicians, medical technicians and staff can experience a large cumulative radiation dosage over time, both directly and indirectly, from conducting many procedures even.

To protect the operator and staff from this radiation, shielding such as lead aprons, gowns, glasses, skirts, etc., is worn. Such lead clothing, especially a lead apron, is quite heavy and uncomfortable, and its use has been associated with cervical and lumbar spine injury.

SUMMARY OF THE INVENTION

Recently, catheter positioning devices have been developed that enable physicians, medical technicians and staff to perform these procedures using a remote controller, thereby helping to reduce exposure to radiation. The various embodiments include systems and components of a catheter positioning device for controlling actuators of the catheter in multiple axes. The catheter positioning system may include a sled member that advances along a sled base. A catheter may be attached to the sled member by a modular plate with one or more actuator interfaces that may couple with the actuators of a catheter handle. One or more motors or drives in the sled member may move the actuator interfaces of the modular plate to control one or more actuators on the catheter in different axes.

In various embodiments the sled member may have a clam shell design in which two or more sides of the sled member close around the catheter handle. Each side of the clam shell sled member may couple with one or more modular plates. The one or more modular plates may have actuator interfaces controlled by motors in the sled member that manipulate control actuators on the catheter handle. In further embodiments, the sled member may include adjustable faces that adjust to fit different types of modular plates and thereby control one or more actuators on different types of the catheter.

Drive linkages in the sled member may be configured to actuate the actuator interfaces about two or more axes, and may be moveable in order to accommodate different types of modular plates. Drive linkages in the sled member may be coupled to a multi-stage interface that may be configured to enable the catheter to be removed from the modular plate of the sled member while maintaining a sterility of the catheter. In such embodiments, a first stage of the interface may be on a first side of a sterility boundary and a second stage of the interface may be on a second side of the sterility boundary. Drive linkages in the sled member may include a translating linkage configured to drive translational movement, a rotating linkage configured to drive rotation about a first axis, and an axial linkage configured to drive rotation about a second axis.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

FIGS. 7A and 7B are side and oblique views, respectively, of a catheter coupled with an embodiment device capable of driving actuators in multiple axes with one motor.

FIGS. 8A and 8B are side and oblique views, respectively, of an alternate catheter coupled with an embodiment device capable of driving actuators in multiple axes with one motor.

FIGS. 9A and 9B are side and oblique views, respectively, of an alternate catheter coupled with an embodiment device capable of driving actuators in multiple axes with one motor.

FIGS. 22A and 22B are alternate views of an embodiment sled member capable of controlling actuators in three different axes with multiple adjustable faces.

DETAILED DESCRIPTION

Figure 1:
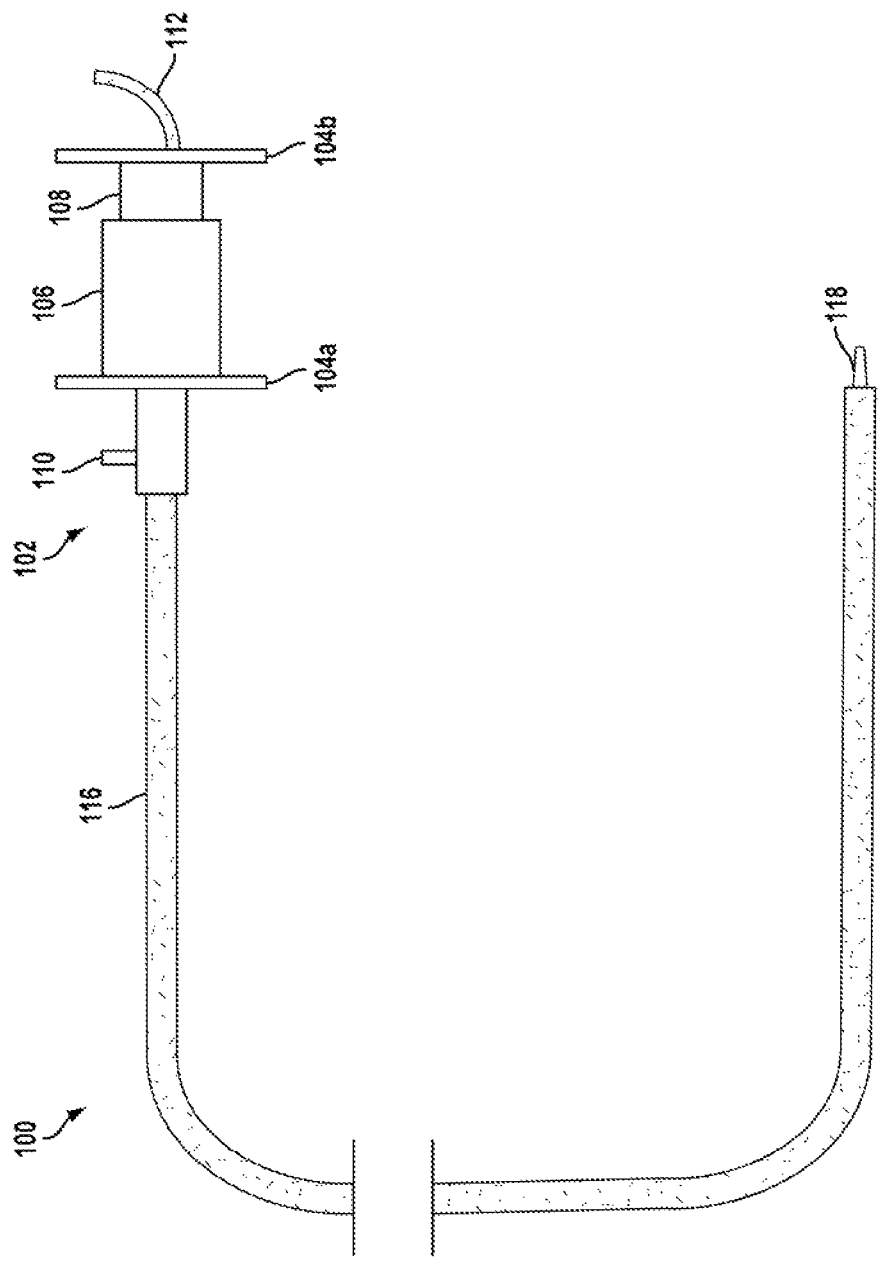
FIG. 1 is a top view of a catheter that could be used in accordance with various embodiments.

Various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the invention or the claims.

Various embodiments provide systems and methods for controlling multiple actuators on a catheter with a catheter positioning device by using a remote controller. A catheter may include a proximal portion or handle that may be fitted or attached to the catheter positioning device. The catheter positioning device may then be used to move the attached catheter, such as advancing or retracting the catheter in relation to a patient or within a patient's body while actuating control levers on the catheter's handle. Catheter actuators may be configured to cause various actions on the catheter, such as deflecting a tip of the catheter to help in navigation of the catheter through a patient or controlling one or more transducers to assist in an operation.

Catheter handles may have multiple actuators configured to control multiple degrees of freedom of the catheter, and each of these actuators may be controlled in a different axis. For example, a catheter handle may have a first actuator that is rotated about a first axis to cause the catheter's tip to bend, a second actuator that is translated along the long axis of the handle to cause a portion of the catheter to expand, and a third actuator that is rotated about a third axis to form a loop in the catheter. A doctor manually using the catheter manipulates these three different actuators to accomplish their respective motions (e.g., turning each of the rotating actuators, pushing or pulling the translating actuator) in the three axes in order to use each actuator and fully control the catheter.

In various embodiments, the catheter positioning device includes components for controlling actuators in multiple axes in order to accommodate catheters with multiple actuators. As described below, the catheter positioning system may include a sled member that advances along a sled base to control a longitudinal position of the catheter in a patient. A catheter may be attached to the sled member by a modular plate that corresponds to the particular type of catheter being used (i.e., different modular plates may be designed to fit the size and shape of catheters from various manufacturers, but every modular plate may attach to the sled member). A modular plate may have one or more actuator interfaces configured to couple with the actuators on a catheter handle. One or more motors or drives in the sled member may move the actuator interfaces of the modular plate to control the one or more actuators on the catheter in different axes. In this way, a user may use the catheter positioning system to remotely control not only the position of the catheter, but also each of the catheter's actuators.

In further embodiments, the sled member may include components configured so that a single motor controls actuators in different axes. For example, the sled member may have gears to transform rotary motion from one motor into motion in multiple axes, such as the motor turns a gear that turns two other gears each about a different axis.

In further embodiments, the modular plate and/or sled member may include adjustable faces that are configured to adjust to fit different types of modular plates and thereby control one or more actuators on different types of the catheter. For example, the sled member may have two faces that move closer together to couple with one type of modular plate and move apart to fit a second a type of modular plate. In further embodiments, a modular plate may include multiple actuator interfaces to couple with different actuators on the catheter handle, and these actuator interfaces may couple with different faces on the sled member.

In further embodiments, the modular plate and/or sled member may include multiple faces that control actuators on different sides of the catheter. For example, in an embodiment the sled member may have a "clam shell" design in which two or more sides of the sled member close around the catheter handle. Each side of the clam shell sled member may couple with one or more modular plates. The one or more modular plates may have actuator interfaces controlled by motors in the sled member and used to control actuators on the catheter handle. In the various embodiments, the catheter contacting surfaces on the components of the sled members may be sterile components, either sterilizable or disposable, to avoid introducing contaminants into the body of a patient.

FIGS. 1-5 illustrate an example prior art catheter and catheter positioning system on which the various embodiment improvements may be implemented. These figures are intended to provide context for the invention described herein and are not intended to limit the scope of the claims. Unlike the prior art system illustrated in FIGS. 1-5, the various embodiments of the invention provide new systems and components for controlling multiple catheter actuators in different axes.

FIG. 1 illustrates an example catheter 100 that may be used with the various embodiments. The catheter 100 may include a handle portion 102 and tube portion 116. The handle portion 102 may be located at a proximal end of the catheter 100 while the distal end of the tube portion 116 may be inserted into the body of a patient.

The handle portion 102 of the catheter 100 may also include an irrigation port 110, which may be used to introduce water or other fluids to lubricate the catheter and ease insertion or retraction in the patient. The handle portion 102 may also include a back port through which one or more wires or cables 112 may leave the handle portion 102. Cables 112 may supply power to the catheter 100 or transmit signals, such as sending commands from a remote controller or other control device to the catheter or relaying data from one or more transducers present on the catheter.

The handle portion 102 may include actuators to control the behavior of the catheter 100. For example, the handle portion 102 shown in FIG. 1 includes a front flange 104a and rear flange 104b that may be squeezed together such that the inner cylinder 108 slides inside the outer cylinder 106. This motion may actuate one or more mechanisms at the tip 118 of the catheter.

In alternate embodiments, various other catheters may be used with different actuators or functions, such as actuators for deflecting the tip of the catheter to ease navigation inside a patient or for controlling one or more transducers at the tip (e.g., electrical leads, one or more sensor devices, ultrasound devices, etc.).

Figure 2:
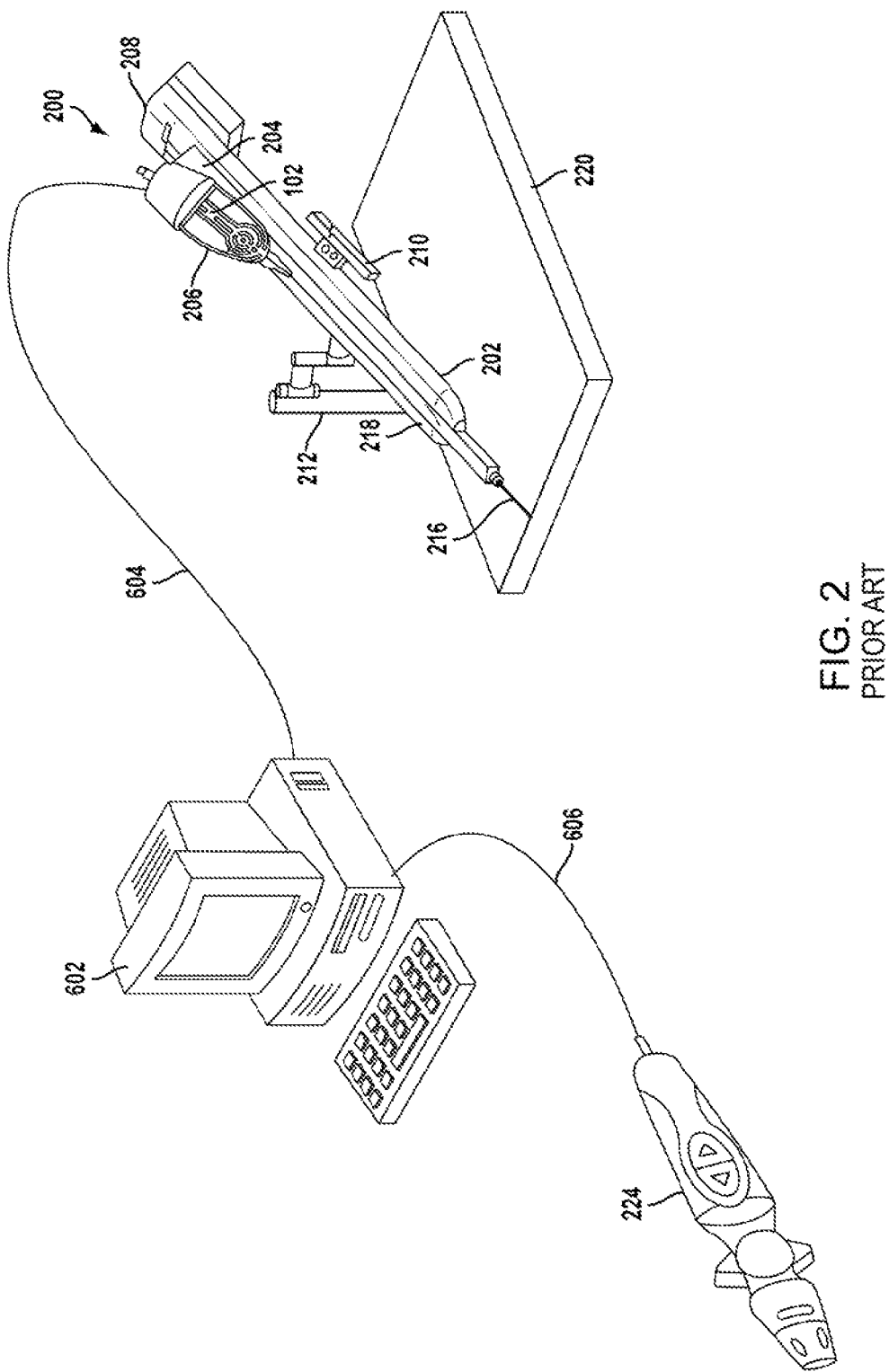
FIG. 2 is a system block diagram of a remote controller, a remotely controlled catheter system, and a programmable control system.

FIG. 2 illustrates a catheter positioning system 200 with a programmable control system 602. A remote controller 224 may be connected to the programmable control system 602 by a wired connector 606 or a wireless data link (not shown). The programmable control system 602 may also be connected to the catheter positioning device 200 by a wired connector 604 or a wireless data link (not shown).

The catheter positioning device 200 may include a sled base 202 coupled with a sled member 204. The sled base 202 may be configured to advance the sled member 204 along the sled base 202 towards the body of the patient or back away from the patient. For example, the sled member may be moved with a motor 208 at one end of the sled base 202. The sled member 204 may move along a rail or other track, such as a worm drive, back and forth along the longitudinal axis of the sled base 202.

The sled base may be mounted with an arm 212, such as over an operating table 220. The arm 212 may be extended or rotated to position the sled base 202 relative to a patient on the operating table 220. The sled base 202 may include a handle 210 to move the sled base 202 into position. The sled base may also include a nose cone 216 that may be inserted into a patient. Alternately, the nose cone 216 may connect with an introducer or sheath that may be inserted into the patient. A catheter may be advanced along the sled base 202 and then through the nose cone 216 into the patient.

The sled base 202 may include a sterile barrier to protect the catheter. In various embodiments, the sterile barrier may include a resealable delivery channel 218 configured to receive and guide the catheter along the sled base as it is advanced by the sled member 204.

The sled member 204 may be equipped with a modular plate 206 to which a catheter handle 102 may be attached. Various embodiments may include many alternate modular plates 206 that may be swapped out so that the catheter positioning system may be used with many different types of catheters. Depending on the kind of catheter that is desired for a procedure, an appropriate modular plate 206 may be attached to the sled member 204 and the catheter may be attached to the module plate 206. The modular plate 206 may also integrate with any actuators on the catheter handle 102, thereby allowing an operator to control the actuators via the remote controller 224.

The sled member 204 may rotate, thereby rotating a catheter connected to the modular plate 206. This rotation may be controlled remotely via the remote controller 224. By controlling translation along the sled base 202, rotation of the sled member 204, and actuation of the catheter's handle via the modular plate 206, an operator may position and actuate the catheter similar to how the catheter would be manually manipulated for a desired operation. Further, an operator may control each of these degrees of freedom (i.e., translation, rotation, and actuation) remotely with the remote controller 224.

The programmable control system 602 may output command signals to the positioning device 200 based on training or programming, such as programmed movements for automatic positioning of the catheter and/or guidewire. Programmed movements of the positioning device may be input prior to a medical procedure, such as by entering commands into the programmable control system 602 (e.g., via a keyboard) or by training the system, such as through manipulation of the remote controller. For example, a user may train the programmable control system to direct the positioning system to execute a series of translation and rotation movements by manipulating the control inputs on the controller as if directing the movements in real time. The programmable control system may store the command inputs and then combine the commands into a single programmed movement, such as in response to an operator selecting a number of pre-trained/programmed movements that should be accomplished in an indicated sequence. Programmed movements may include various combinations of the commands, such as simultaneously rotating and translating the system to create a "corkscrew" maneuver. These programmed movements may be triggered later by a single input, such as a user identifying the sequence by a file name or preset program and pressing an execute key on the controller or the system keyboard.

Figure 3:
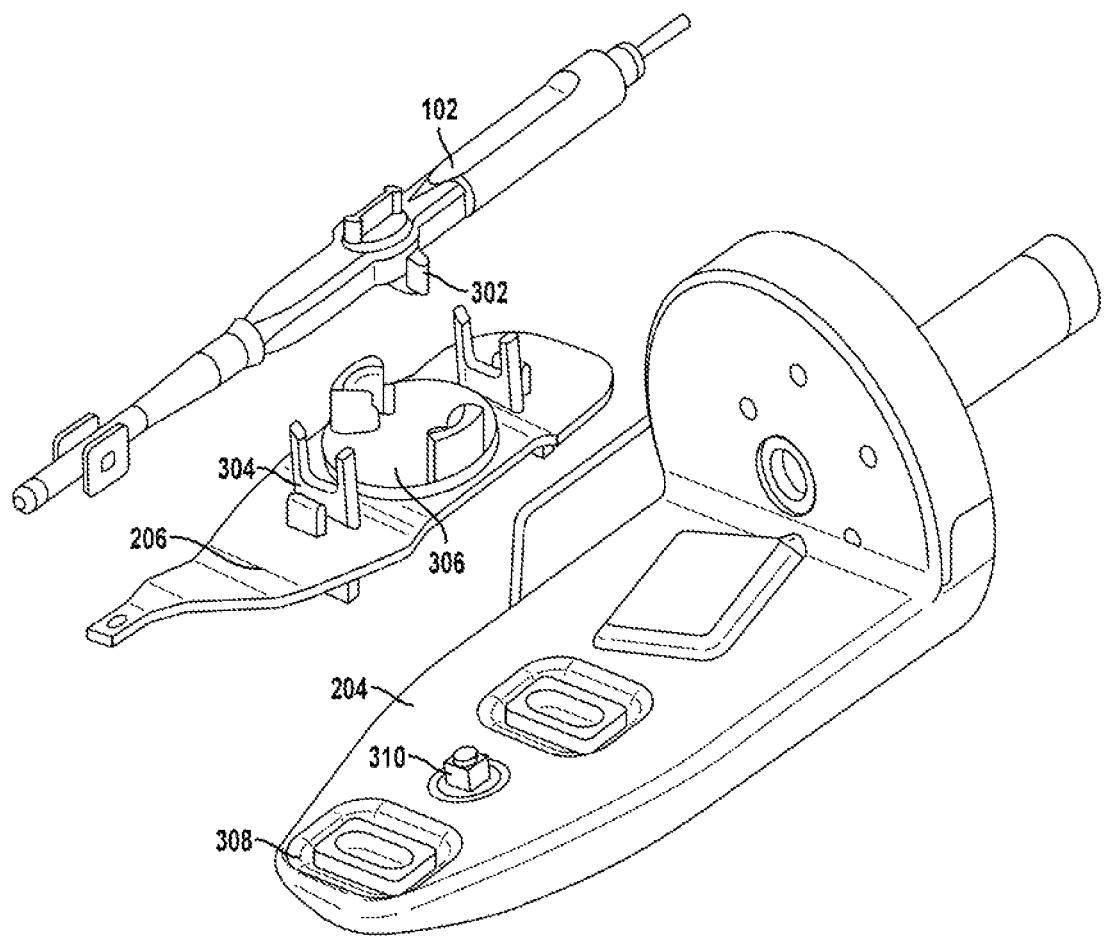
FIG. 3 is an exploded view of a catheter handle portion, a modular plate, and a sled member according to various embodiments.

FIG. 3 illustrates an exploded view of a catheter handle 102, modular plate 206, and sled member 204. The catheter handle 102 may include one or more actuators 302. FIG. 3 illustrates a catheter handle 102 with a rotatable lever as opposed to the flanges 104a and 104b shown in FIG. 1. As discussed above, the modular plate 206 may be swapped out so that various catheters with different actuators may be connected to the catheter positioning device. FIG. 3 illustrates a modular plate 206 that includes clamps 304 to secure the catheter handle 102, as well as a molded nest 306 configured to integrate with the actuator 302 (i.e., the rotatable lever may be controlled by rotating the molded nest 306).

The modular plate 206 may be rigidly connected to the sled member 204 such that translation or rotation of the sled member is transferred through the modular plate 204 to the catheter handle 102 to drive and position the catheter. The sled member 204 and modular plate 206 may be connected by one or more detachable joints 308, such as a socket into which a part of the modular plate 204 may plug. The sled member 204 may also include a linkage 310 to integrate with the modular plate 206. The linkage 310 may allow the operator to control the catheter's actuators 302, such as by controlling the molded nest 306. The linkage 310 may be configured to integrate with any of the various modular plates 204 designed to connect with different catheter handles. In various embodiments, the linkage 310 may be a simple element (such as a rotational element shown in FIG.

3) that can drive one or more catheter specific control devices of the modular plate (e.g., driving the molded nest 304 configured for a particular type of catheter handle 102).

Figure 4:
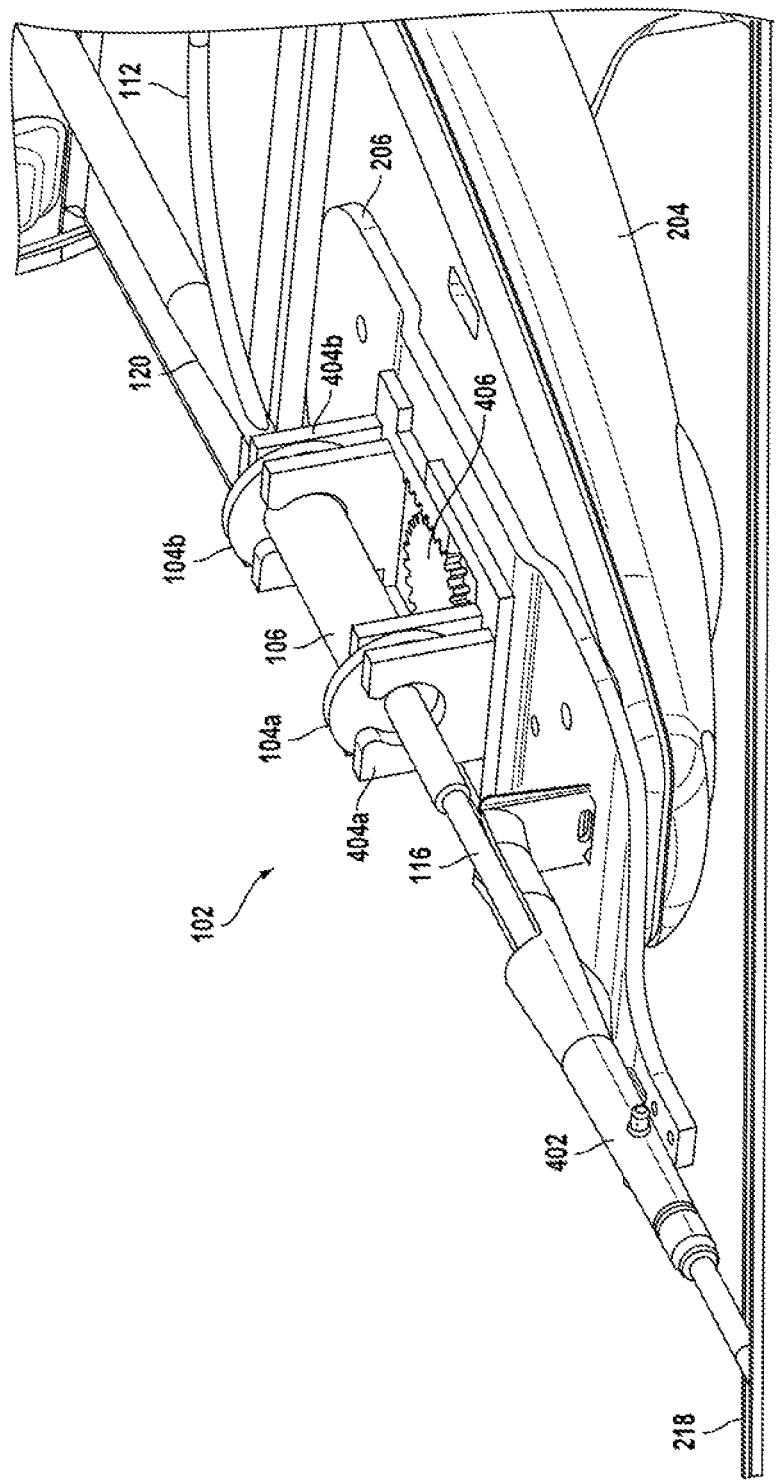
FIG. 4 is an oblique view of a catheter handle portion, a modular plate, and a sled member coupled together according to various embodiments.

FIG. 4 illustrates an example embodiment in which the catheter of FIG. 1 is connected with the modular plate 206 and sled member 204. The modular plate 206 may include clamps 404a and 404b for securing the catheter handle's flanges 104a and 104b. The modular plate 206 may also include a gear 406 that may rotate to translate toothed arm 408 to move the clamps 404a and 404b. As shown in FIG. 4, the gear 406 may have teeth that mesh with teeth on a drive arm 408 extending from one or both clamps 404a and 404b such that rotation of the gear 406 is converted into a translation motion of one or both clamps 404a and 404b. The gear 406 may be controlled from underneath by a linkage 310 (not visible in FIG. 4) on the sled member 204 that may be rotated in response to commands from the remote controller.

By moving the clamps 404a and 404b together, the flanges 104a and 104b may be squeezed together to drive an inner cylinder 108 (not visible in FIG. 4) into an outer cylinder 106 and thereby actuate a certain catheter function.

The modular plate 206 may be attached to an introducer 402, which may lead the catheter's tube portion 116 into the resealable delivery channel 218. As the sled member 204 is advanced, the end of the introducer 402 may stay inside the resealable delivery channel 218 by moving between the plastic lips of the resealable groove.

The catheter handle 102 may include a back port that may have one or more cables or tubes 112 that are led back, such as through the sled member 204.

Figure 5:
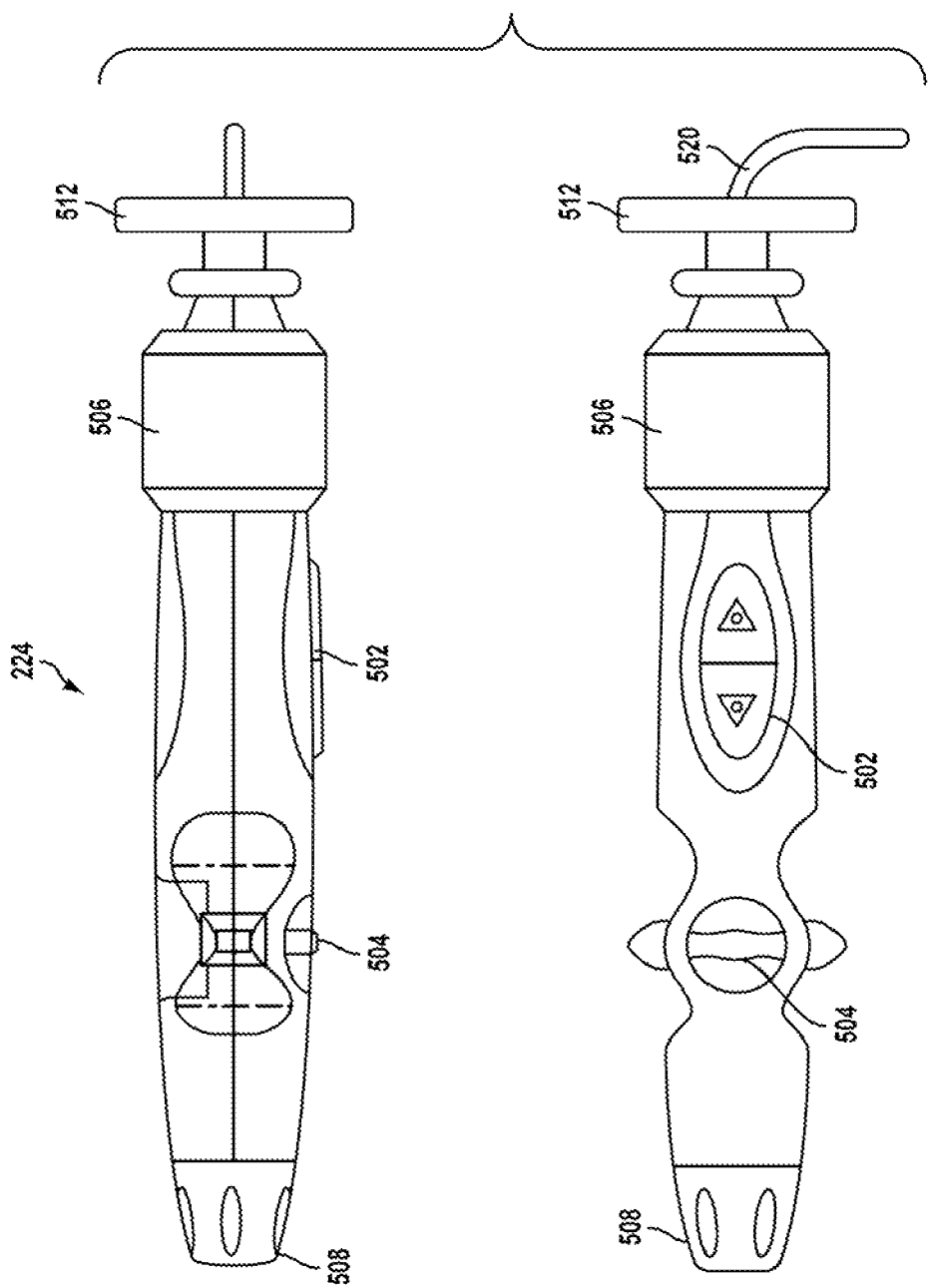
FIG. 5 is a top and side view of a remote controller in accordance with an embodiment of the invention.

FIG. 5 illustrates a remote controller 224 from a side and top perspective that may be used to control the catheter positioning system. The remote controller 224 may include buttons 502 for controlling the forward and backward motion of a catheter provided by sliding the sled member 204 up or down the sled base 202. The remote controller 224 may include a dial 508 at one end for controlling rotation of the catheter by rotating the sled member 204. Control signals may be sent from the remote controller 224 to the catheter positioning device via a wire 520 or wirelessly via a transmitter (not shown).

The remote controller 224 may also include a rotatable knob 504 that may send control signals to the sled member to control actuation of one or more actuators on the catheter handle 102. For example, rotation of rotatable knob 504 may correspond to rotation of the gear 406 to move the catheter handle's front flange 104a and rear flange 104b and extend the laser tip 118. In another example embodiment, rotation of the rotatable knob 504 may correspond to rotation of a molded nest on the modular plate to rotate a catheter handle's actuator and result in deflection of a distal tip of the catheter.

The remote controller 224 may also include a rotatable sleeve 506 that may be rotated to provide another user input. Rotation of this sleeve 506 may be transmitted to the sled member 204 to control a drive motor to control rotational motions applied to a rotatable sleeve or other actuator on the catheter handle 102. In an example embodiment, rotation of the rotatable sleeve 506 may result in deflection of a distal tip of the catheter in a plane perpendicular to the plane of deflection of the distal tip controlled by the rotatable knob 504. Rotation of the rotatable sleeve 506 may alternatively be translated into other control actions, such as changing the size or shape of a distal portion of the catheter.

The remote controller may also include a push pull user input device 512 that may similarly be configured to control actuation of another catheter element. For example, in or out movement of the push pull user input device 512 may correspond to translational movements applied to a push pull actuator on the catheter handle 102. In an alternate example embodiment, pushing or pulling the push pull user input device 512 may result in changing the diameter of a loop (or other shape change feature) on the distal tip of the catheter.

Figure 6A:
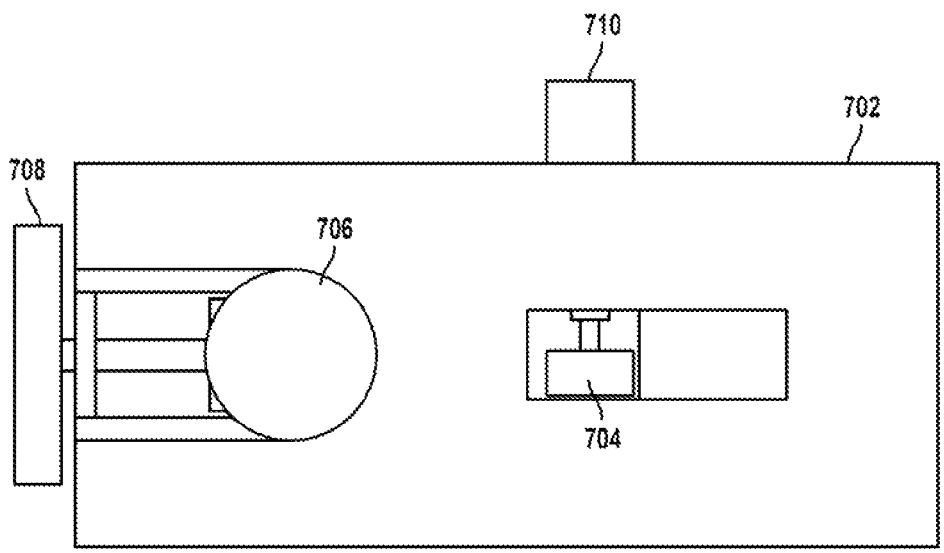
FIGS. 6A, 6B, and 6C are a top, side, and rear view, respectively, of an embodiment device capable of driving actuators in multiple axes with one motor.
Figure 6B:
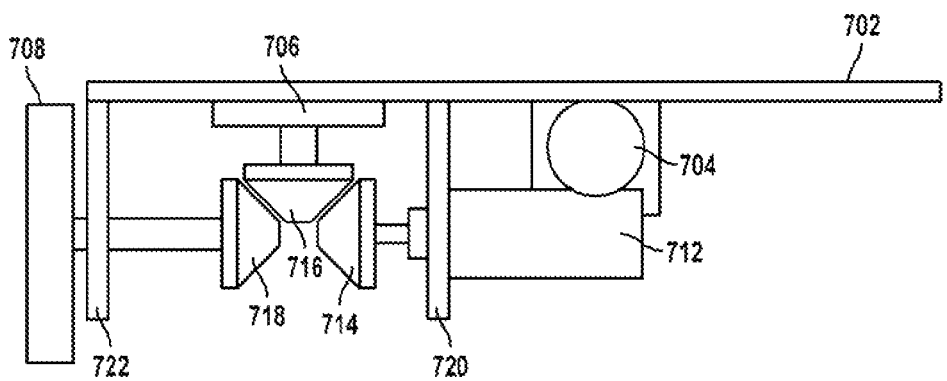
Figure 6C:
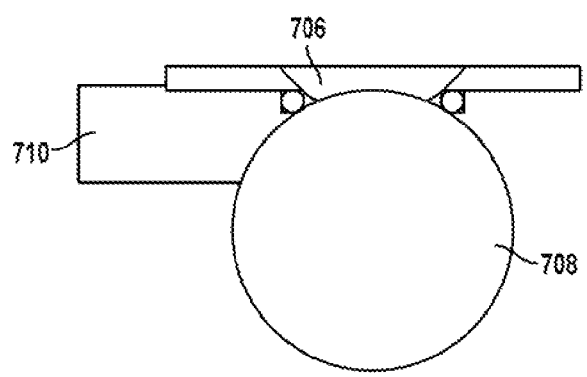

In various embodiments, the catheter positioning device may include components for controlling actuators in multiple axes. For example, FIGS. 6A, 6B, and 6C illustrate three views of part of an embodiment sled member that includes multiple linkages configured to drive actuators in three axes and therefore may accommodate a wide range of catheters such as catheters with single actuators but in different axes, as well as catheters with multiple actuators. The embodiment sled member may also be more efficient, cost effective, and easy to use by employing a single motor to control multiple actuators in different axes. In the various embodiments, the catheter contacting surfaces on the components of the sled members may be sterile components, either sterilizable or disposable, to avoid introducing contaminants into the body of a patient. For example, modular plates that interface with the catheter may be sterile or sterilizable.

The sled member 702 components may include a first motor 712 that drives a first gear 714. The first gear 714 may be a bevel gear paired with a second gear 716 attached to a first linkage 706. The second gear 716 may also be a bevel gear and may be paired with a third gear 718 attached to and configured to drive a second linkage 708.

As the first motor 712 drives the first gear 714 that gear drives the second gear 716 and third gear 718, which in turn may drive the first linkage 706 and the second linkage 708, respectively. The first linkage 706 may rotate in a different axis than the second linkage 708 and together may provide control over catheter actuators in multiple axes.

Each linkage may be configured to transfer motion from a motor to another component. The first and second linkages 706, 708 may couple with actuator interfaces on a modular plate, and the actuator interfaces may couple with actuators on a catheter handle. Thus, the first motor 712 may indirectly drive catheter actuators on the modular plate via the linkages 706, 708 and the actuator interfaces.

In various embodiments, the sled member components may also include additional motors and/or linkages, such as a second motor 710 that may drive a third linkage 704. In FIGS. 6A, 6B, and 6C, the second motor 710 drives only one linkage 704, but in alternate embodiments, the second motor 710 or additional motors may drive two linkages like the first motor 712 described above, or more than two linkages.

FIGS. 7A, 7B, 8A, 8B, 9A, 9B, illustrate various catheters with various different actuators being controlled by the embodiment sled member described above with reference to FIGS. 6A-6C.

FIGS. 7A, 7B, 8A, 8B, 9A, and 9B do not include the modular plate in order to more clearly show the linkages and actuator interfaces. These drawings illustrate how the linkage and actuator arrangements of the embodiment illustrated in FIGS. 6A-6C can support a variety of different types of catheters with corresponding modular plates. However, it should be understood that the actuator interfaces may be part of a modular plate used to secure the catheter to the sled member. Examples with modular plates are discussed later and illustrated in subsequent figures.

Figure 7A:
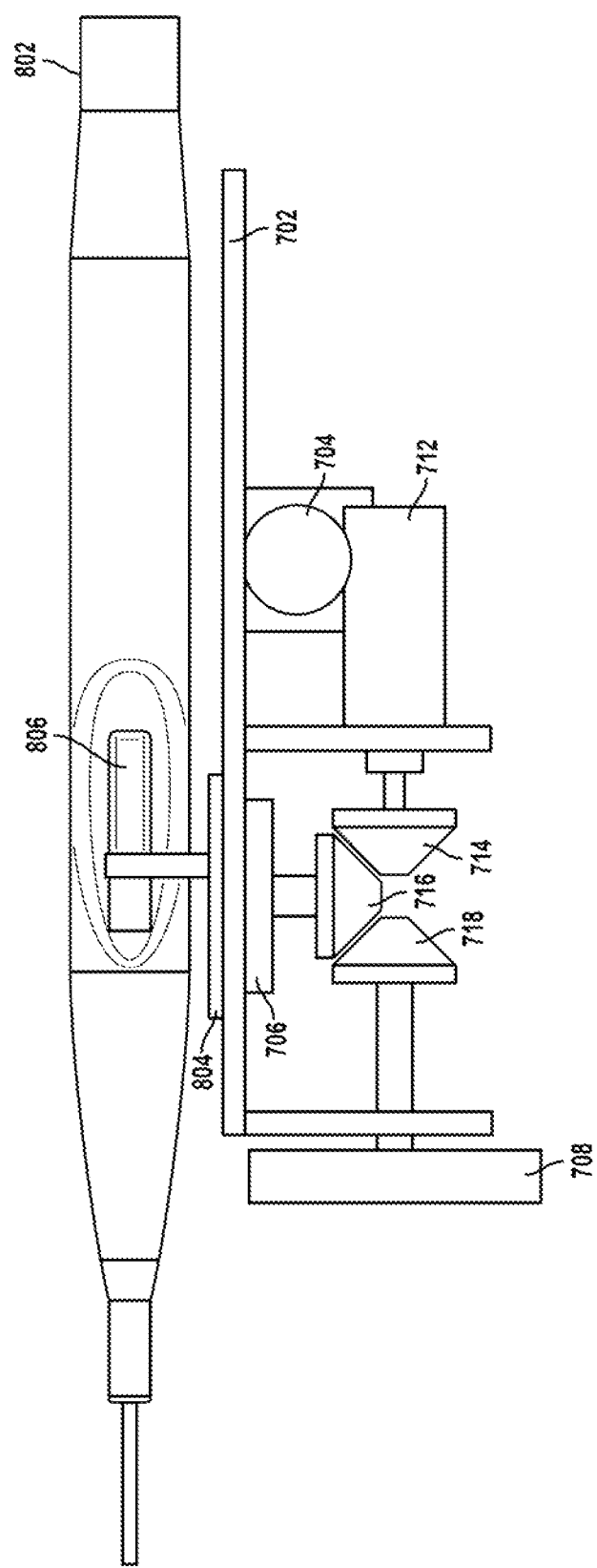

FIGS. 7A and 7B illustrate a catheter 802 including a rotatable actuator 806 can be controlled by the sled member 702 components. The first linkage 706 may rotate an actuator interface 804 to rotate the actuator 806. In this way, a user may remotely control the first motor 712 to drive the first gear 714, which drives the second gear 716 and rotates the first linkage 706, the actuator interface 804, and ultimately the catheter actuator 806. The motor 712 may spin in either direction, and so the actuator interface 804 may rotate and turn the actuator 806 in either direction.

Because the catheter 802 in FIGS. 7A and 7B has only a single actuator, the second linkage 708 and third linkage 704 may not be coupled with catheter actuators on a modular plate. The third gear 718 may be driven as the motor 712 drives the second gear 716 and first linkage 706. Alternately, the third gear 718 may disengage from the other gears, such as retracting or otherwise moving out of contact with the second gear 716.

Figure 8A:
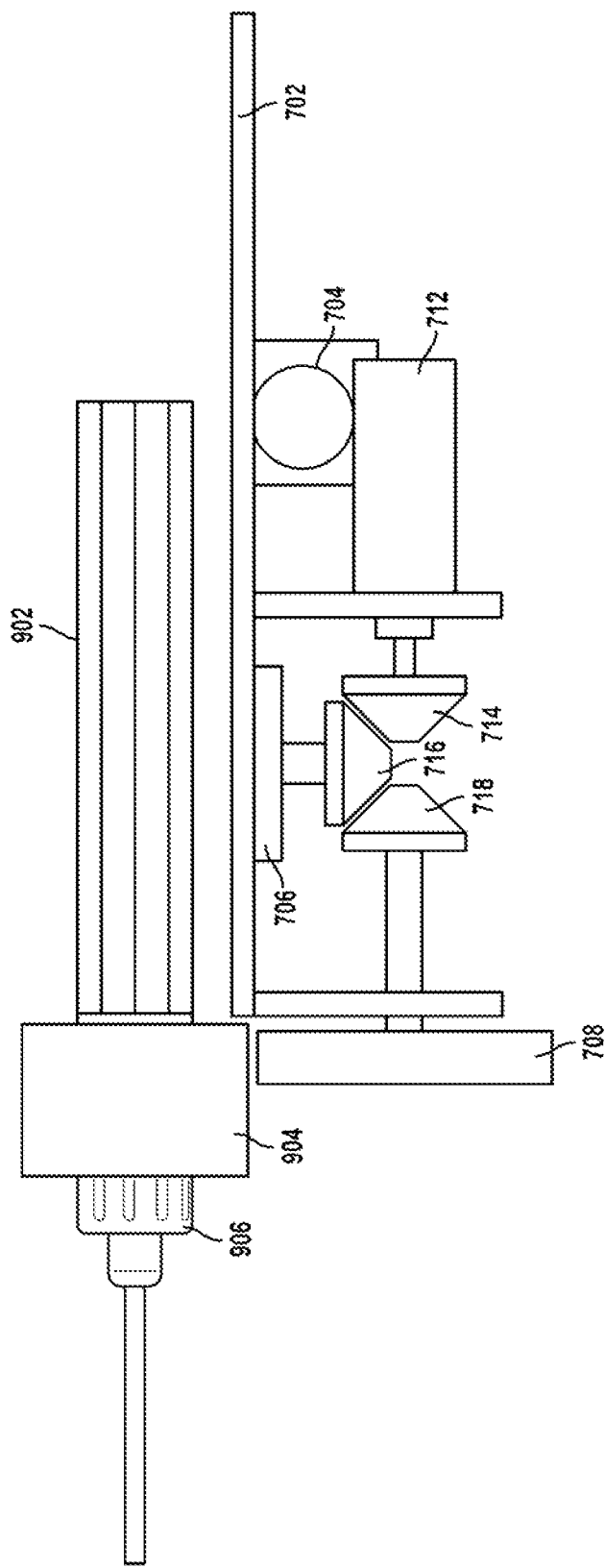

FIGS. 8A and 8B illustrate a different type of catheter 902 controlled by the sled member 702 components. This catheter 902 includes a rotatable actuator 906 that rotates about a different axis than the actuator 802 in FIGS. 7A and 7B. As described above, the first motor 712 may drive a bevel gear 714 that drives gears 716, 718, which drive the second linkage 708, which may rotate a second actuator interface 904 to rotate the catheter actuator 906. The first linkage 706 and third linkage 704 may not be coupled with actuator interfaces in this example because the catheter 902 does not have an actuator to drive in their axes of motion.

Figure 9B:
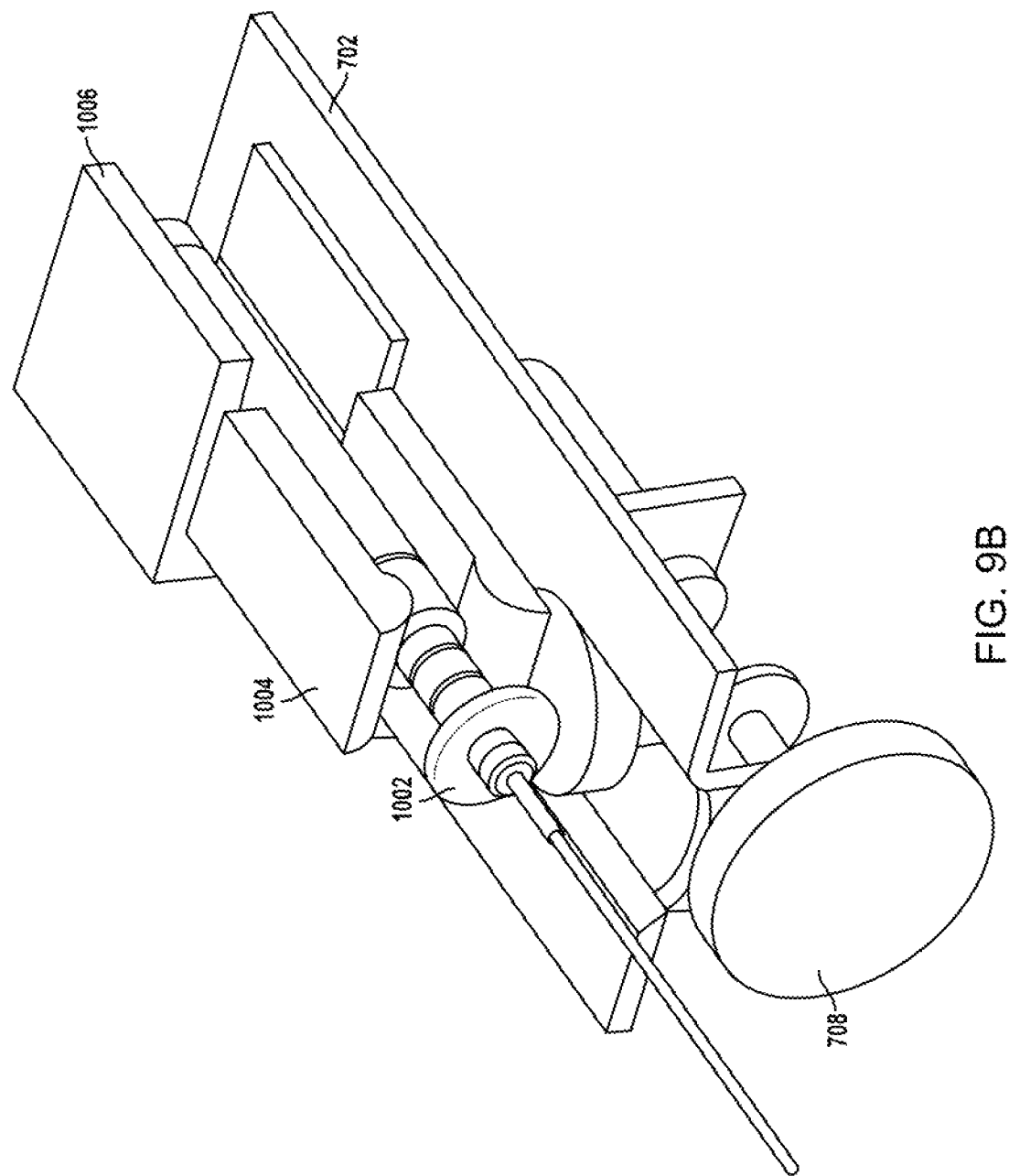

FIGS. 9A and 9B illustrate a third type of catheter 1002 controlled by the sled member 702 components in which the catheter handle includes a translating actuator 1006 that extends and retracts, similar to the catheter shown in FIG. 1. In this implementation, the third linkage 704 driven by the second motor 710 (not visible in FIGS. 9A and 9B, see FIG. 6A) drives a third actuator interface 1004 to translate the actuator 1006 while a support 1008 holds another part of the catheter 1002 in place. With this example catheter the first linkage 706 and second linkage 708 are not coupled to actuator interfaces because the catheter 1002 does not have an actuator to drive in their axes of motion. Therefore the first motor 712 and the gears 714, 716, 718 may not be active when a catheter of this design is being used.

Figure 10:
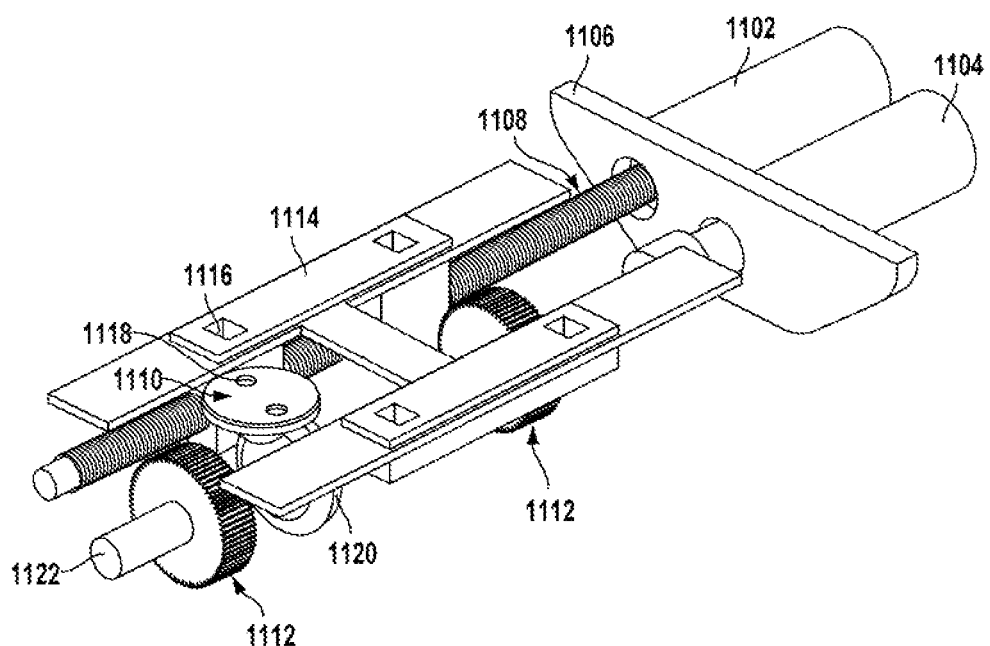
FIG. 10 is an oblique view of an embodiment sled member capable of controlling actuators in three different axes.

FIG. 10 illustrates an alternate embodiment of drive motor and gearing components of a sled member. In this embodiment, the sled member may have a first drive 1102 and a second drive 1104 coupled to a drive support 1106. The first drive 1102 may control a lead screw 1108 used for providing linear action. A translating linkage 1114 may include a drive nut (not visible) interacting with the lead screw to cause the translating linkage to translate back and forth along the length of the lead screw 1108 as the first drive 1102 rotates the lead screw 1108. The translating linkage 1114 may have one or more sockets 1116 for attaching other components, such as parts of a modular plate that move and control a catheter actuator.

The second drive 1104 may rotate an axle 1122 coupled to one or more axial linkages 1112 so that they rotate with the axle 1122. A bevel gear 1120 may also rotate with the axle 1122 and drive a rotating linkage 1110 about a different axis (e.g., perpendicular to the axle 1122). The rotating linkage may have one or more sockets 1118 for attaching other components, such as parts of a modular plate that move and control a catheter actuator.

Figure 11A:
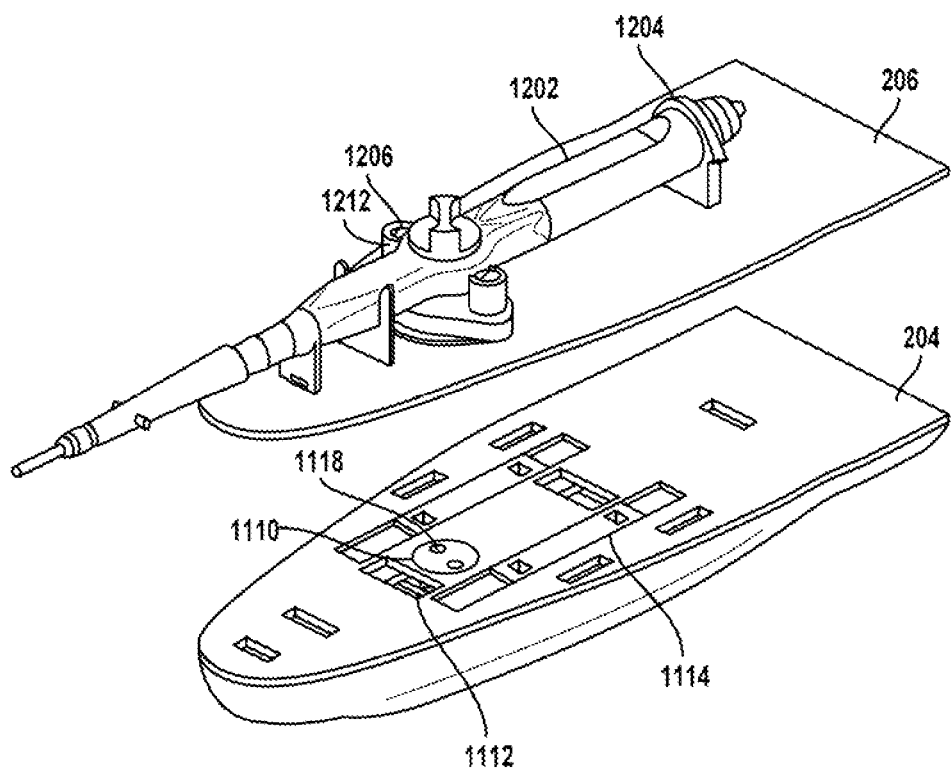
FIGS. 11A, 11B and 11C are oblique views of a catheter coupled with an embodiment modular plate and components of the embodiment sled member of FIG. 10.
Figure 11B:
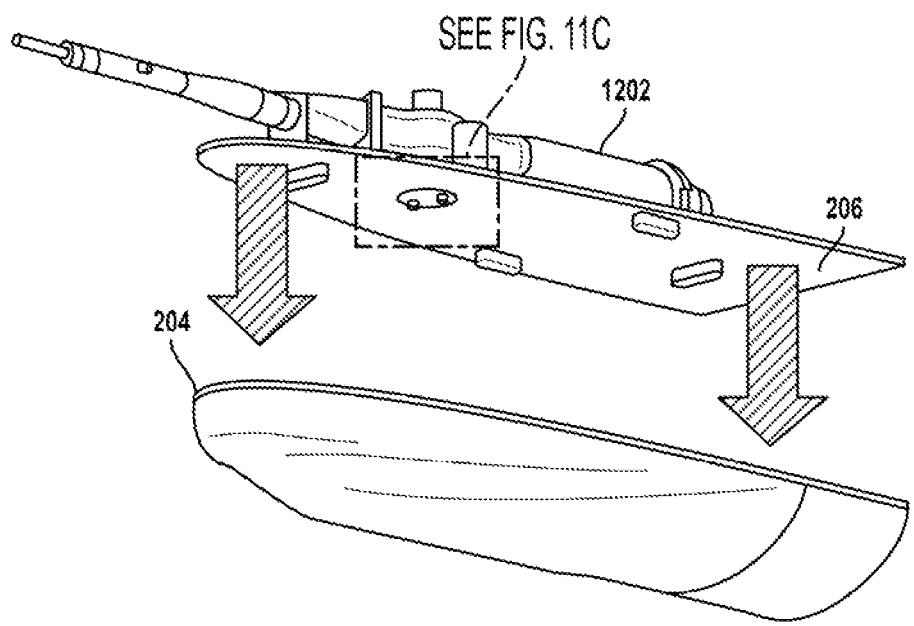
Figure 11C:
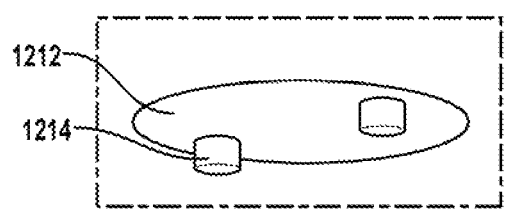

FIGS. 11A, 11B, and 11C illustrate this embodiment of the sled member components along with an interfacing modular plate 206 connected to a catheter 1202. As discussed above, the catheter 1202 may be coupled to a modular plate 206 and held in place by one or more clamps 1204. The illustrated catheter 1202 has a rotatable actuator 1206 that fits into an actuator interface 1212 (e.g., molded nest) that is part of the modular plate 206.

The sled member 204 includes the three linkages 1110, 1112, 1114 described above with reference to FIG. 10, with the actuator interface 1212 featuring projections 1214 (e.g., FIG. 11C) configured to couple with sockets 1118 of the rotating linkage 1110 in the modular plate 206 when the modular plate is connected with the sled member. Once the modular plate is connected to the sled member and the catheter handle is coupled to the modular plate, the second drive 1104 may rotate the axle 1122 and the bevel gear 1120 which in turn may rotate the rotating linkage 1110 to rotate the actuator interface 1212, which rotates the actuator 1206 on the catheter handle 1202.

Figure 12:
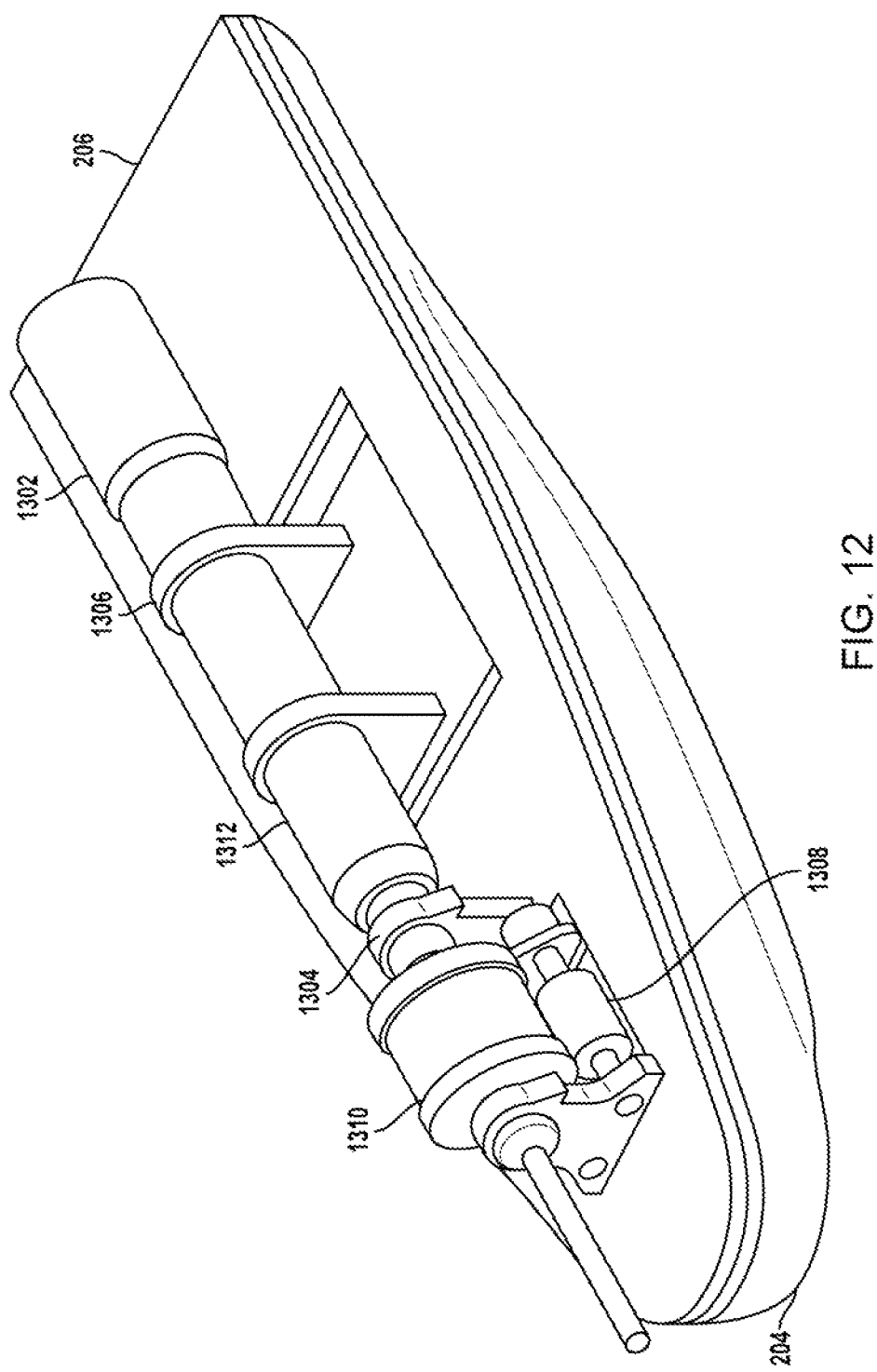
FIG. 12 is an oblique view of an alternate catheter coupled with an embodiment modular plate and components of the embodiment sled member of FIG. 10.

FIG. 12 illustrates another example embodiment and a different catheter 1302 featuring a rotating actuator 1310 and a translating actuator 1312. The catheter 1302 may be coupled to a modular plate 206 and held in place by one or more clamps 1304. The modular plate 206 may couple with the sled base 204 such that linkages (not visible in FIG. 12) can drive moving parts (i.e., actuator interfaces) of the modular plate 206. A rotating actuator interface 1308 may be driven by a linkage (e.g., an axial linkage 1112) and may rotate the rotating actuator 1310. A translating actuator interface 1306 may be driven by a linkage (e.g., a translating linkage 1114) and may slide the translating actuator 1312 back and forth. The clamps 1306 or other support on the modular plate 206 may hold the catheter steady as the actuators 1312, 1310 are moved.

Figure 13A:
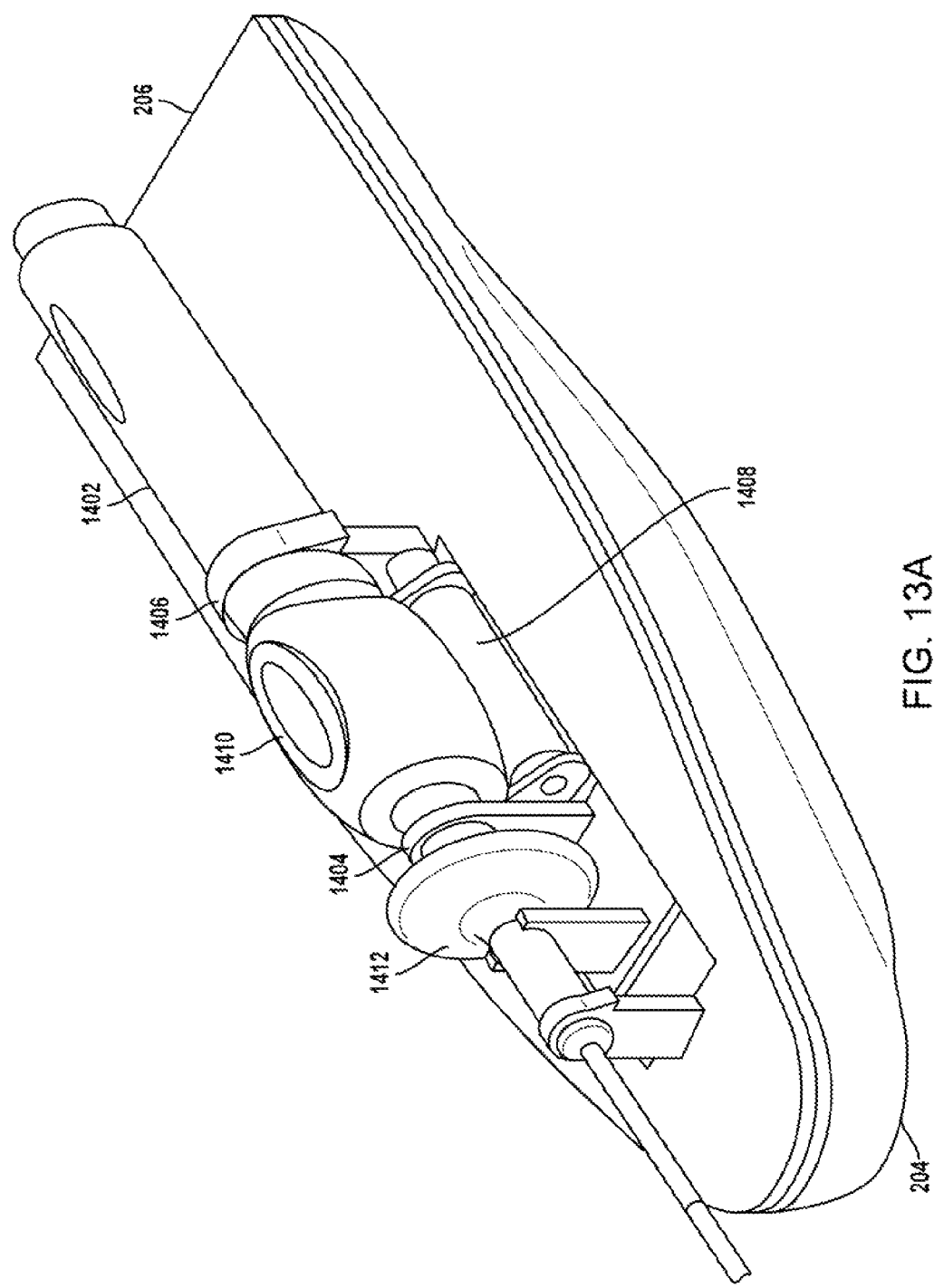
FIGS. 13A and 13B are oblique views of an alternate catheter coupled with an embodiment modular plate and components of the embodiment sled member of FIG. 10.
Figure 13B:
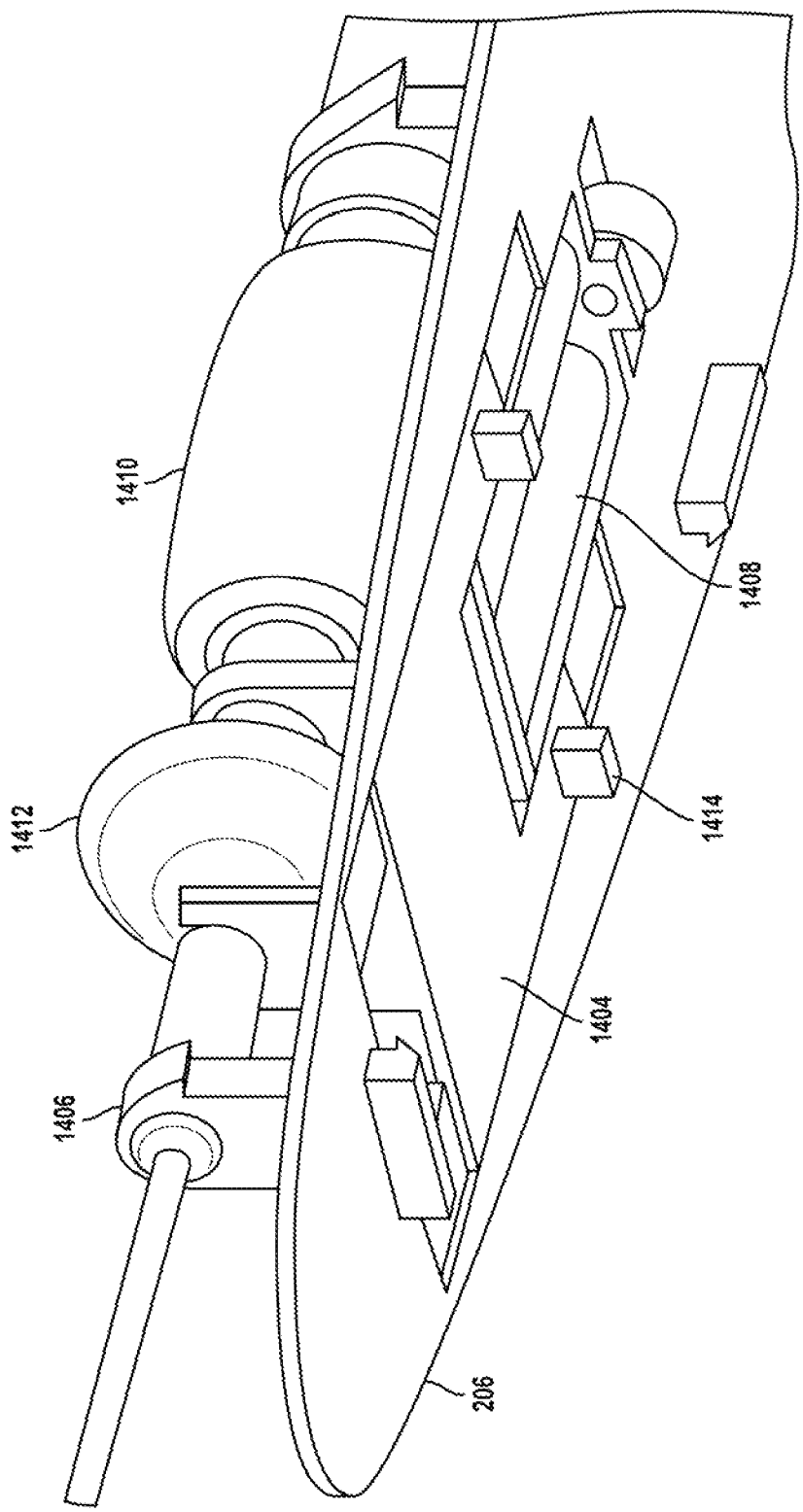

FIGS. 13A and 13B illustrate another embodiment and a third type of catheter 1402 with a differently positioned rotating actuator 1410 and translating actuator 1412. The catheter 1402 may be coupled to a modular plate 206 and held in place by one or more clamps 1406. The modular plate 206 may couple with the sled base 204 such that linkages (not visible in FIGS. 13A and 13B) can drive moving parts (i.e., actuator interfaces) of the modular plate 206. A rotating actuator interface 1408 may be driven by a linkage (e.g., an axial linkage 1112) and may rotate the rotating actuator 1410. As illustrated in FIG. 13B, the rotating actuator interface 1408 may extend below the modular plate 206 to engage a linkage of the sled member 204.

A translating actuator interface 1404 may be driven by a linkage (e.g., a translating linkage 1114) and may slide the translating actuator 1412 back and forth. The translating actuator interface 1414 may have one or more protrusions 1414 to couple with a linkage of the sled member 204. The clamps 1406 or other support on the modular plate 206 may hold the catheter 1402 steady as the actuators 1410, 1412 are moved.

Figure 14A:
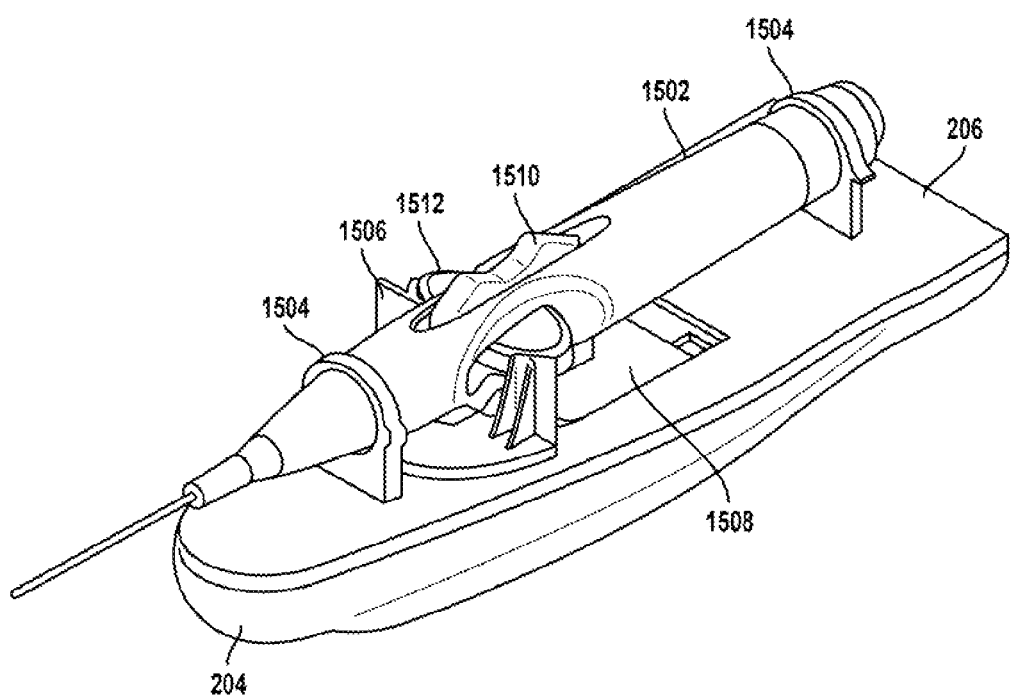
FIGS. 14A and 14B are oblique views of an alternate catheter coupled with an embodiment modular plate and components of the embodiment sled member of FIG. 10.
Figure 14B:
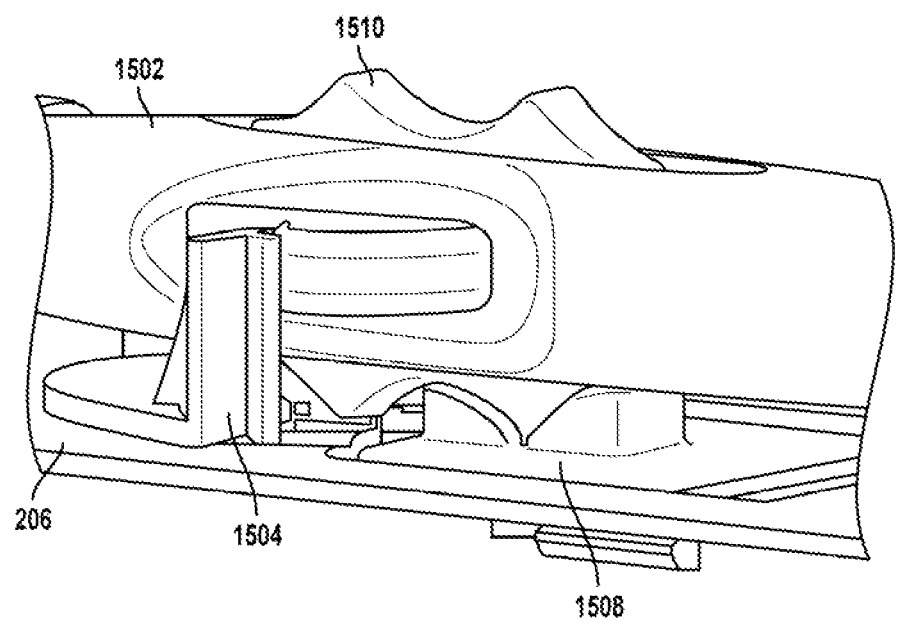

FIGS. 14A and 14B illustrate an example embodiment with a fourth type of catheter 1502. The catheter 1502 may be coupled to a modular plate 206 and held in place by one or more clamps 1504. The catheter 1502 may have a rotatable actuator 1512 and a translatable actuator 1510. The modular plate 206 may have a rotating actuator interface 1506 configured to control the rotatable actuator 1512 and a translating actuator interface 1508 configured to control the rotatable actuator 1510. The rotating actuator interface 1506 and translating actuator interface 1508 may be configured to couple with linkages (not shown) of the sled member 204.

Figure 15A:
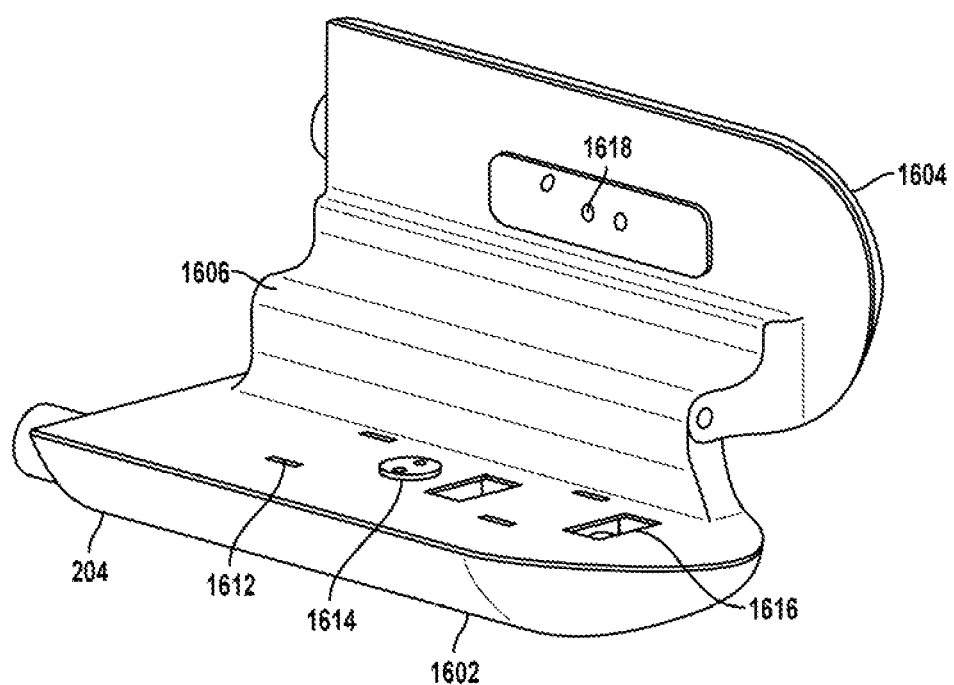
FIGS. 15A-15C are alternate views of an embodiment clam shell sled member in different configurations.
Figure 15B:
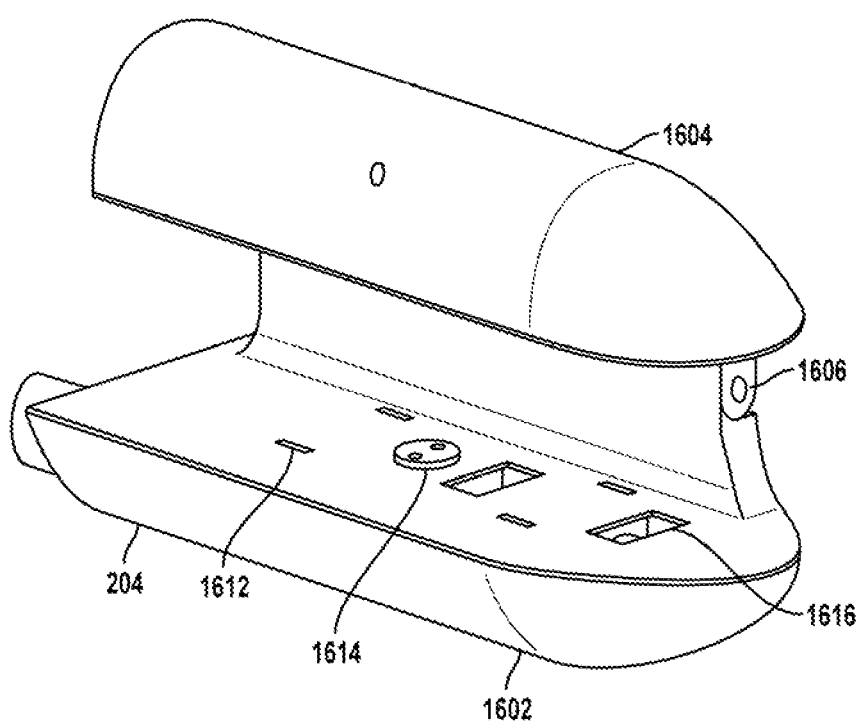
Figure 15C:
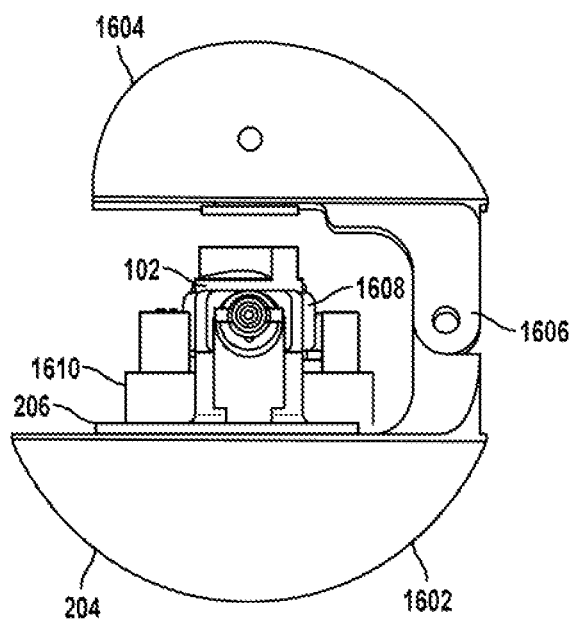

In further embodiments, the modular plate and/or sled member may include multiple faces that control actuators on different sides of the catheter. For example, in various embodiments the sled member may have a "clam shell" design in which two or more sides of the sled member close around the catheter handle to engage all actuators. FIGS. 15A, 15B, and 15C illustrate an example embodiment sled member 204 with a clam shell shape having a bottom portion 1602 and a top portion 1604 joined by a hinge joint 1606.

In various embodiments, the bottom portion 1602 or top portion 1604 may be configured to couple with the same modular plates and catheters as single face sled members. However, a clam shell sled member may be coupled with more types of catheters than single face sled members. The clam shell shape may provide more volume for including additional linkages. The clam shell shape also can provide additional linkages to support modular plates with actuator interfaces to couple with actuators on two sides of the catheter handle. For example, an actuator on the bottom of the catheter handle may be engaged by an actuator interface on the bottom portion 1602 and an actuator in the top of the catheter handle may be engaged by an actuator interface on the top portion 1604 of the clam shell, or on a second modular plate coupled to the top portion of the clam shell.

FIG. 15A illustrates the sled member in an open position, and FIG. 15B illustrates the sled member in a closed position. The bottom portion 1602 may include three linkages 1612, 1614, 1616 in three different axes similar to the sled members discussed above, although more or fewer linkages may be provided. The top portion 1604 may include additional linkages, such as another linkage 1618 as illustrated. In some embodiments, the linkage 1618 may be a linear or rotating linkage.

FIG. 15C illustrates how a clam shell sled member may close around a catheter handle 102 attached to the sled member 204 by a modular plate 206. In this example, the catheter handle 102 may include a single actuator 1608 controlled by an actuator interface 1610.

Figure 16A:
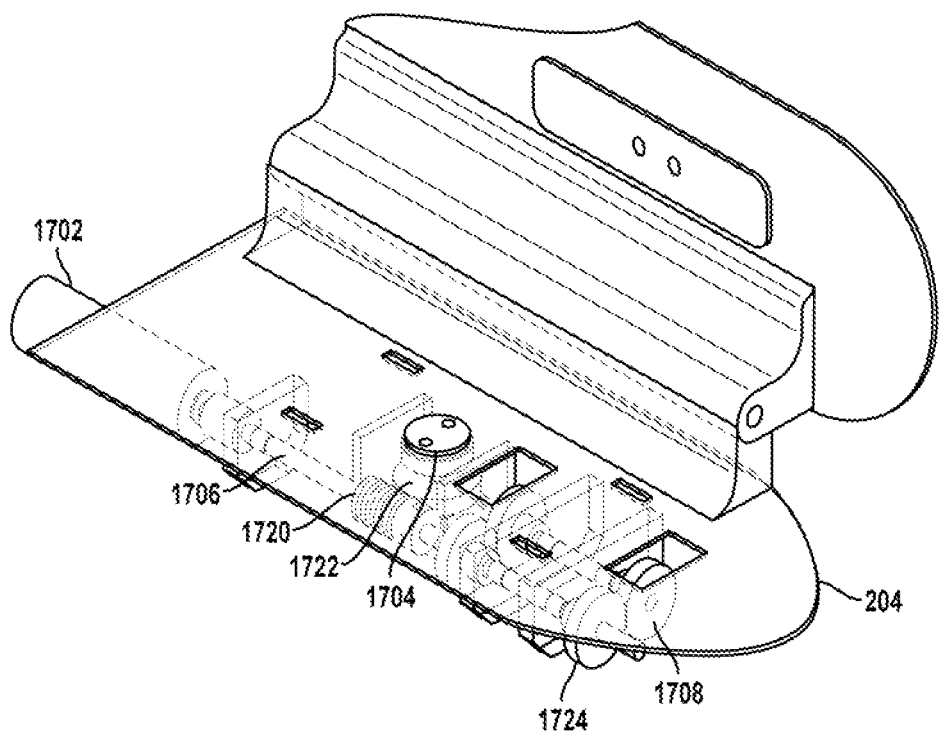
FIGS. 16A and 16B are oblique views of an embodiment clam shell sled member with motors and linkages.
Figure 16B:
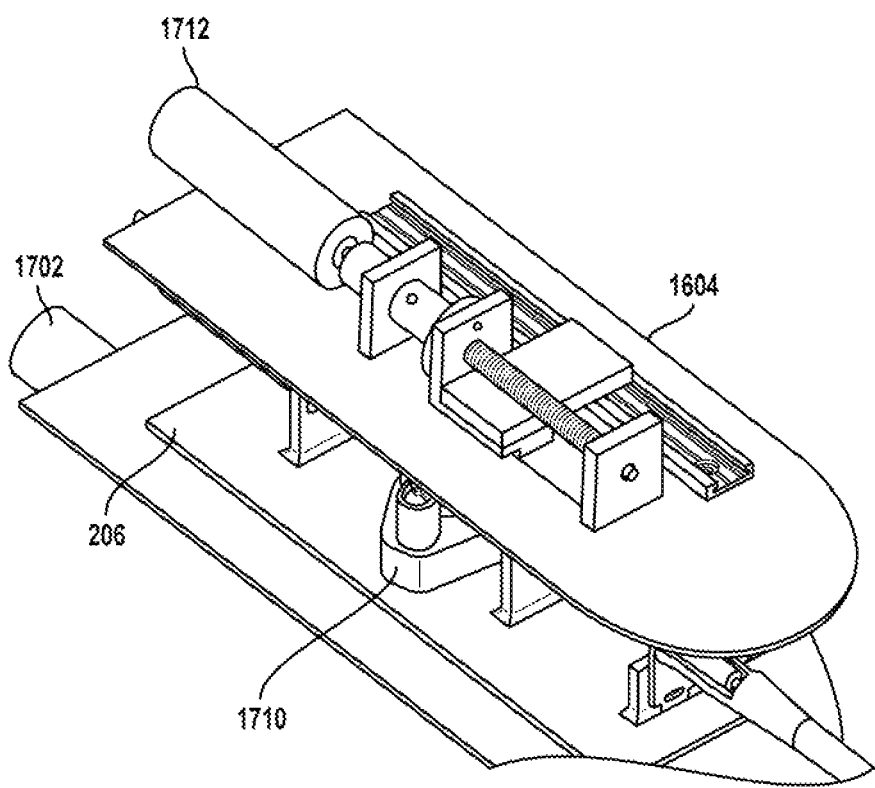

FIGS. 16A and 16B provide a cutaway view of a clam shell sled member 204 showing an embodiment configuration of drive motors and linkages. In an embodiment, a first motor 1702 may be coupled to and drive an axle 1706 that drives one or more axial linkages 1708, either directly or via a gear 1724, to transfer motion to the axial linkage 1708. The axle 1706 may also drive another linkage 1704 rotating in a different axis, such as through a gear 1722 turned by a threaded portion 1720 on the axle 1706.

As shown in FIG. 16B, a modular plate 206 with an actuator interface 1710 configured to be coupled with the sled member. The actuator interface 1710 may be driven by one of the linkages (e.g., rotating linkage 1704). The top portion 1604 of the sled member may have a second motor 1712 configured to drive other linkages (e.g., linkage 1618 shown in FIG. 15B).

Figure 17A:
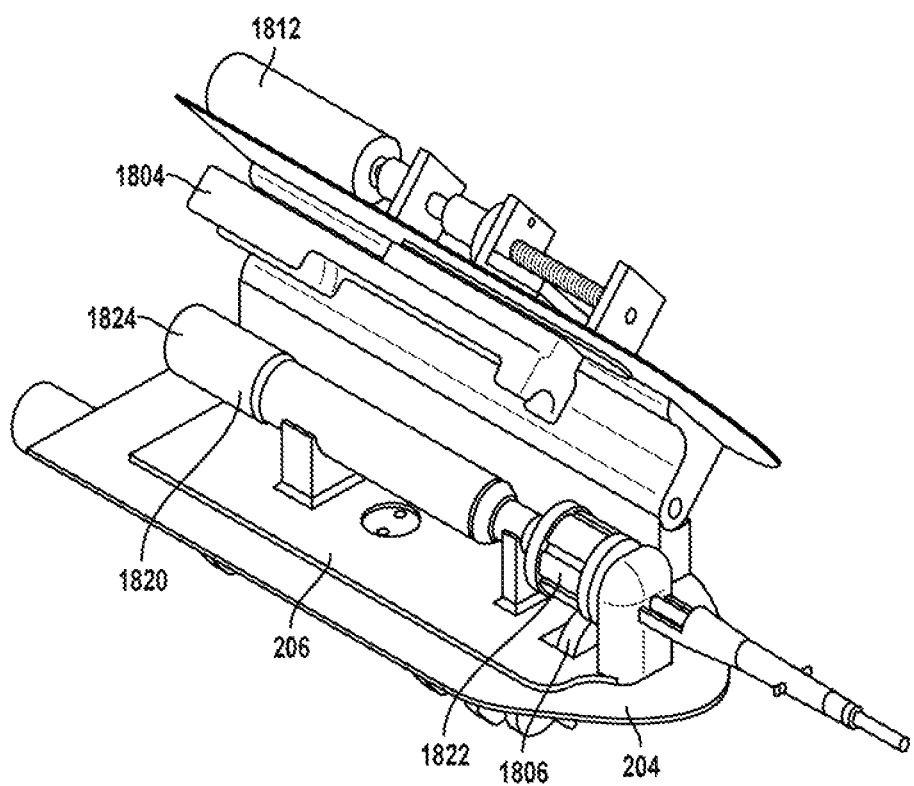
FIGS. 17A and 17B are alternate views of a catheter coupled with an embodiment clam shell sled member and modular plate.
Figure 17B:
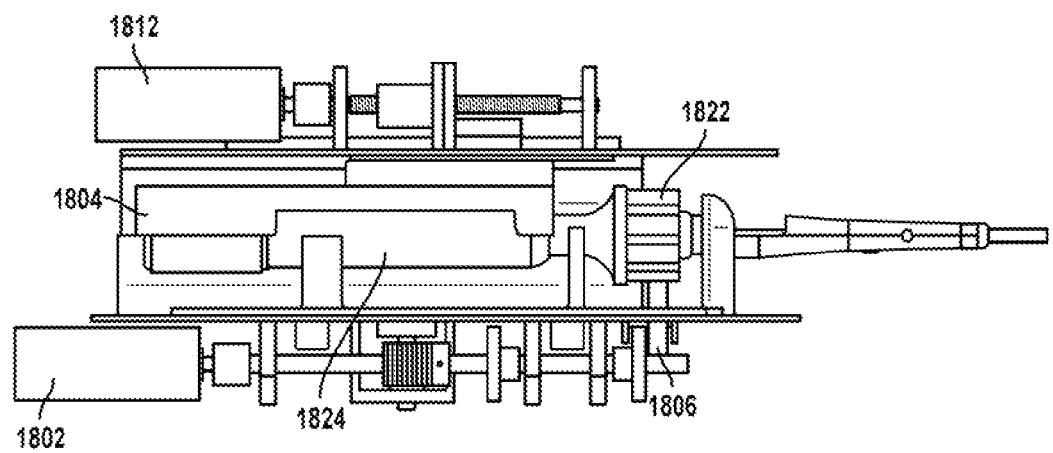

FIGS. 17A and 17B illustrate an example embodiment clam shell sled member 204 with modular plates and a catheter with an axial actuator 1822 and translating actuator 1824. The catheter may be attached to a first modular plate 206 with an axial actuator interface 1806 which may be driven by a linkage, such as an axial linkage shown in FIG. 16A, and which may drive the axial actuator 1822.

When the clam shell sled member is closed, as shown in FIG. 17B, a translating actuator interface 1804 may couple with the translating actuator 1824. The translating actuator interface 1804 may be coupled to the upper portion of the sled member, such as by a second modular plate (not shown) or directly to the upper portion of the sled member. A second motor 1812 may drive a linkage to drive the translating actuator interface 1804 and control the translating actuator 1824.

Figure 18A:
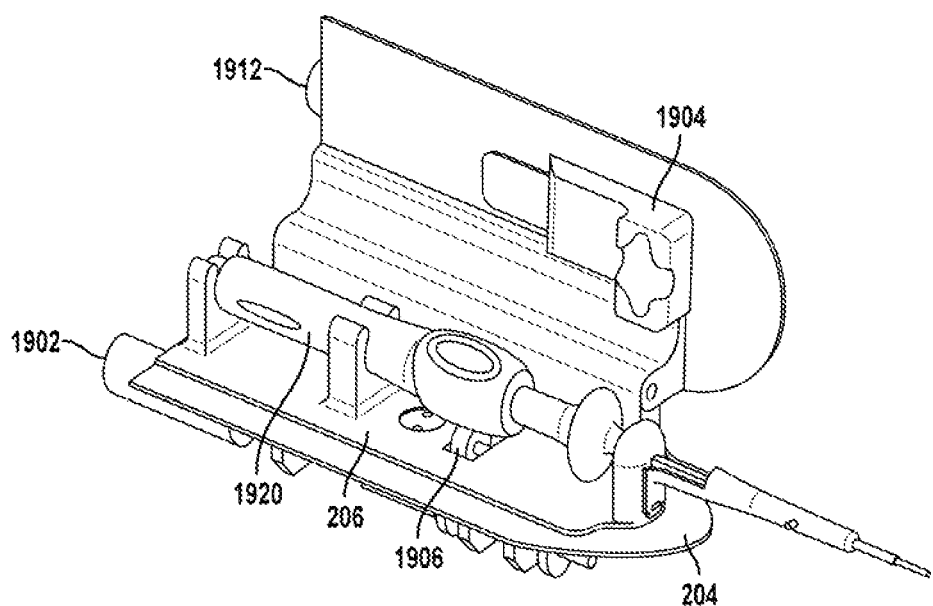
FIGS. 18A and 18B are oblique views of an alternate catheter coupled with an embodiment clam shell sled member and modular plate.
Figure 18B:
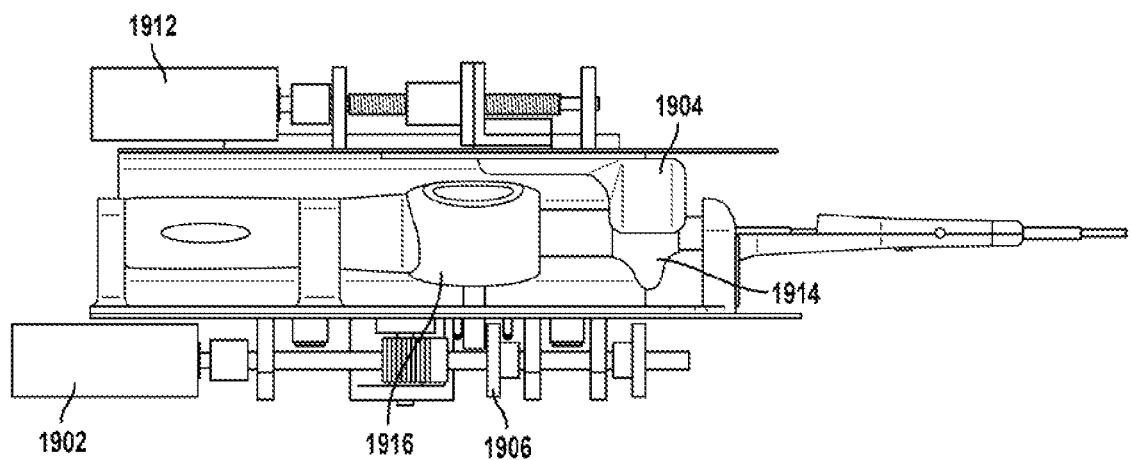

FIGS. 18A and 18B illustrate an embodiment clam shell sled member mated with a different catheter 1920 featuring a translating actuator 1914 and an axial actuator 1916. The catheter may be attached to a modular plate 206 with an axial actuator interface 1906 which may be driven by a linkage, such as an axial linkage shown in FIG. 16A, and which may drive the axial actuator 1916.

When the clam shell sled member is closed, as shown in FIG. 18B, a translating actuator interface 1904 may couple with the translating actuator 1914. The translating actuator interface 1904 may be coupled to the upper portion of the sled member, such as by a second modular plate (not shown) or directly to the upper portion of the sled member. A second motor 1912 may drive a linkage to drive the translating actuator interface 1904 and control the translating actuator 1914.

Figure 19A:
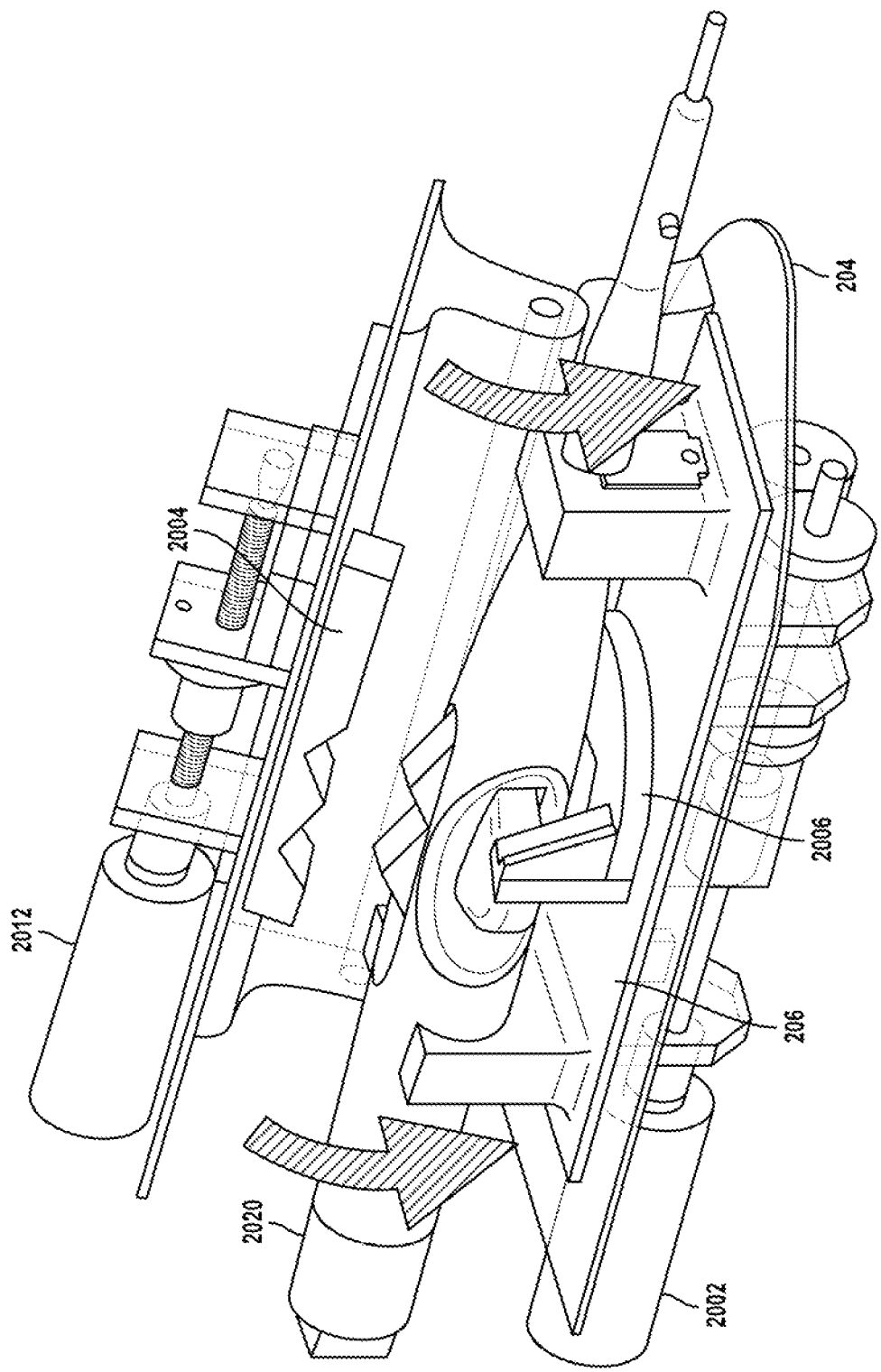
FIGS. 19A and 19B are oblique views of an alternate catheter coupled with an embodiment clam shell sled member and modular plate.
Figure 19B:
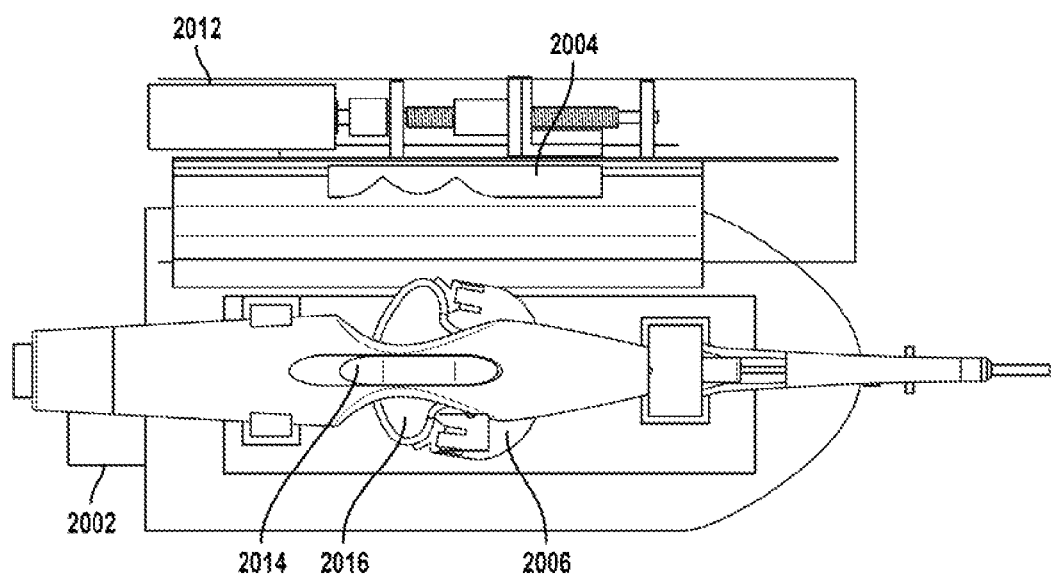

FIGS. 19A and 19B illustrate an embodiment clam shell sled member mated with a different catheter 2020 featuring a translating actuator 2014 and a rotating actuator 2016 on a different axis than the axial actuators discussed above. The catheter may be attached to a modular plate 206 having a rotating actuator interface 2006 which may be driven by a linkage, such as a rotating linkage 1704 shown in FIG. 16A, and which may drive the rotating actuator 2016. A user may remotely control a first motor 2002 to drive the linkage, actuator interface 2006, and rotating actuator 2016.

The clam shell sled member may have a translating actuator interface 2004 which may be coupled to the upper portion of the sled member, such as by a second modular plate (not shown) or directly to the upper portion of the sled member. A second motor 2012 may drive a linkage to drive the translating actuator interface 2004 and control the translating actuator 2014.

Figure 20A:
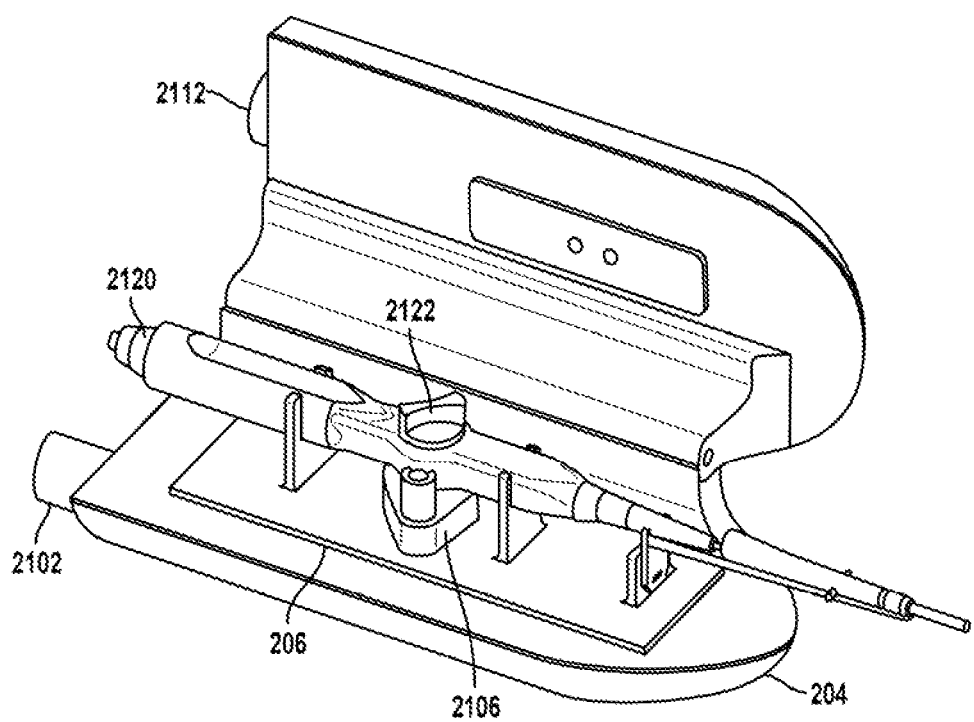
FIGS. 20A and 20B are oblique views of an alternate catheter coupled with an embodiment clam shell sled member and modular plate.
Figure 20B:
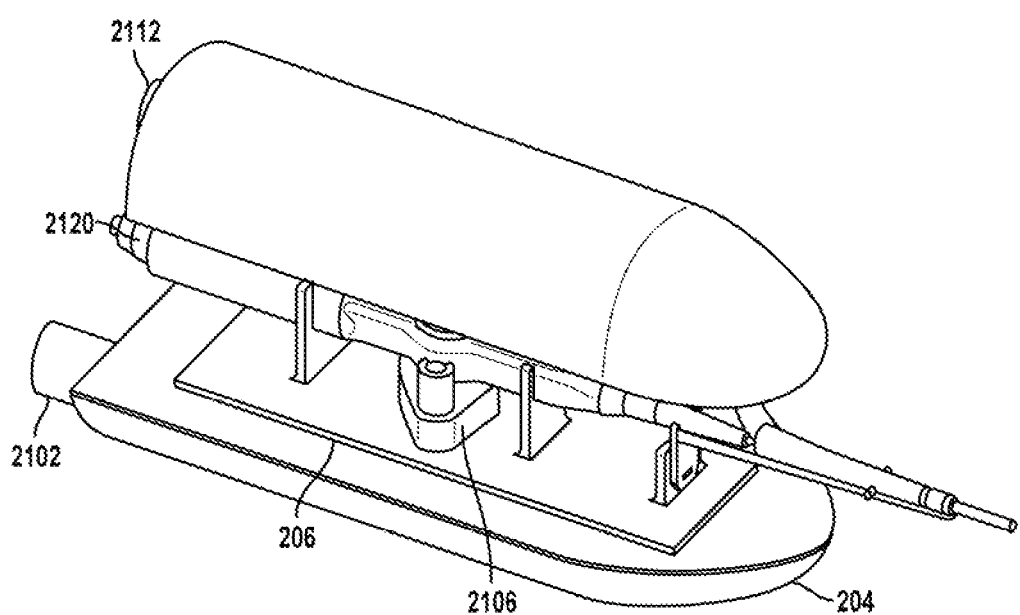

FIGS. 20A and 20B illustrate an embodiment clam shell sled member mated with a different catheter 2120 featuring a rotating actuator 2122. The catheter may be attached to the sled member 204 by a modular plate 206 having a rotating actuator interface 2106. The rotating actuator interface 2106 may be driven by a linkage, such as a rotating linkage 1704 shown in FIG. 16A, and may drive the rotating actuator 2122. A user may remotely control a first motor 2102 to drive the linkage, actuator interface 2106, and rotating actuator 2122.

A second motor 2112 may not be needed to control the catheter if all actuators are controlled by the first motor. For example, the catheter in FIGS. 20A and 20B only has a single actuator controlled by the first motor 2102, so the second motor 2112 may not necessarily be used and no additional interfaces or modular plate may be attached to the upper portion of the clam shell interface.

The catheters discussed in the embodiments above are meant only as examples. Other catheters with any number of different actuators may be used with suitable modular plates to interface with an embodiment clam shell sled member. In further embodiments, each portion of the clam shell sled member may have two or more linkages. Also, separate modular plates may provided for each of the two sides of the clam shell sled member to accommodate different designs of catheter handles. Thus, for catheters that do not require an actuator on a top surface, no modular plate may be implemented on the upper portion of the clam shell, as illustrated in FIG. 20A.

In further embodiments, the sled member may include multiple linkages in the same axis that may adjust to fit different types of modular plates and thereby support one or more actuators for interfacing with different types of catheters. Unlike the clam shell design discussed above, the multiple linkages in the same plane may translate (i.e., move side to side or back and forth) within the plane thereby enabling the sled member to reposition one or both linkages to line up with actuator interfaces in a modular plate. Adjustable multiple linkages may be more versatile than stationary interfaces and may allow more modular plates and catheters to be coupled with the system. Adjustable multiple linkages may also provide more flexibility for designing modular plates to fit new catheters developed in the future.

Figure 21:
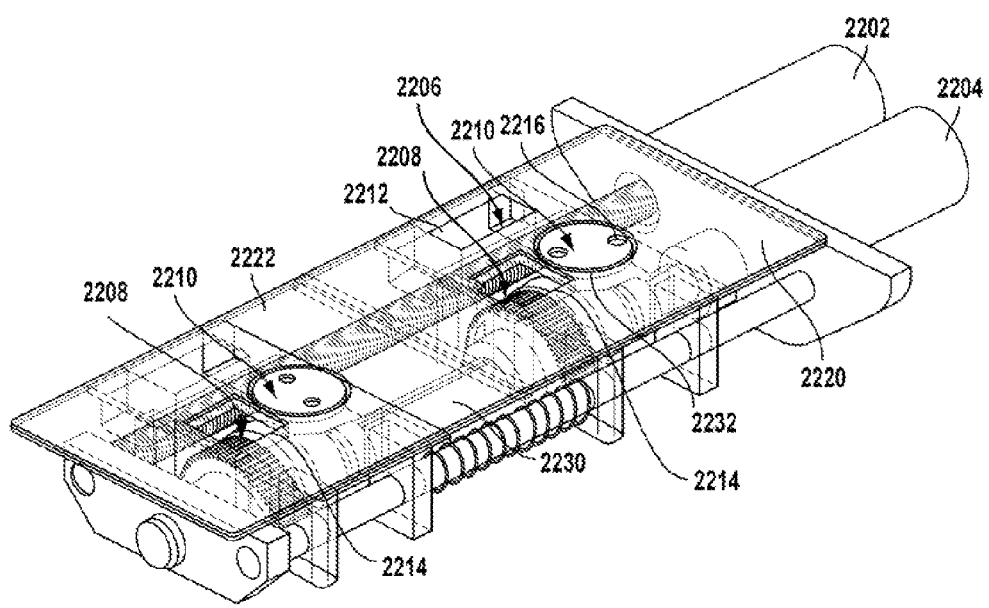
FIG. 21 is an oblique view of components of an embodiment sled member capable of controlling actuators in three different axes with multiple faces.

FIG. 21 illustrates components of an embodiment sled member with a first linkage 2220 and a second linkage 2222. The sled member may have a first drive 2202 and a second drive 2204 coupled to the two linkages, respectively. For example, the first drive 2202 may rotate a lead screw 2206 used for linear action. Each of the linkages may have an opening 2212 to allow components, such as actuator interfaces of modular plates, to access the lead screw 2206. For example, an actuator interface on a module plate may have a threaded portion that reaches down and meshes with the threads of the lead screw in the sled member such that the linkage translates back and forth as the first drive 2202 rotates the lead screw 2206.

The second drive 2204 may rotate an axle 2230 to turn one or more axial linkages 2208. Each of the faces may have an opening 2214 to allow components, such as actuator interfaces of modular plates, to access and mesh with the axial linkages 2208.

Each of the multiple linkages in the sled member may also have a rotating linkage 2210 that rotates in a different axis than the axle 2230. The rotating linkages 2210 may each be connected to a gear 2232 meshing with the axle 2230 such that the gears 2232 and rotating linkages 2210 rotate with the axle 2230. The rotating linkage 2210 may have one or more sockets 2216 for attaching other components, such as an actuator interface of a modular plate. In further embodiments, the axle may be a splined shaft and may mesh with a bevel gear to turn the rotating linkages.

In various embodiments, the first linkage 2220 and second linkage 2222 may be adjusted to fit a particular modular plate or actuator. For example, the first face 2220 or second face 2222 may translate or move back and forth along the sled member. Each of the linkages may still function after this adjustment. The lead screw 2206 may still be accessible through an opening 2212 to drive translating components. The axial linkages 2208 may move up and down the axle with the first face 2220 or second face 2222. The rotating linkages 2210 may also move with the first face 2220 or second face 2222 and still be driven by the axle. For example, the axle may be a splined shaft and the splines may remain meshed with the linkage's bevel gear. Alternately, a bevel gear may move along the axle with the rotating linkage.

In alternate embodiments, the multiple linkages in a sled member may be repositioned by rotating or translating in other directions than along the long axis of the sled member. In various embodiments, each actuator interface may be repositioned separately, such as repositioning one interface while the other remains stationary or adjusting each interface differently.

Figure 22A:
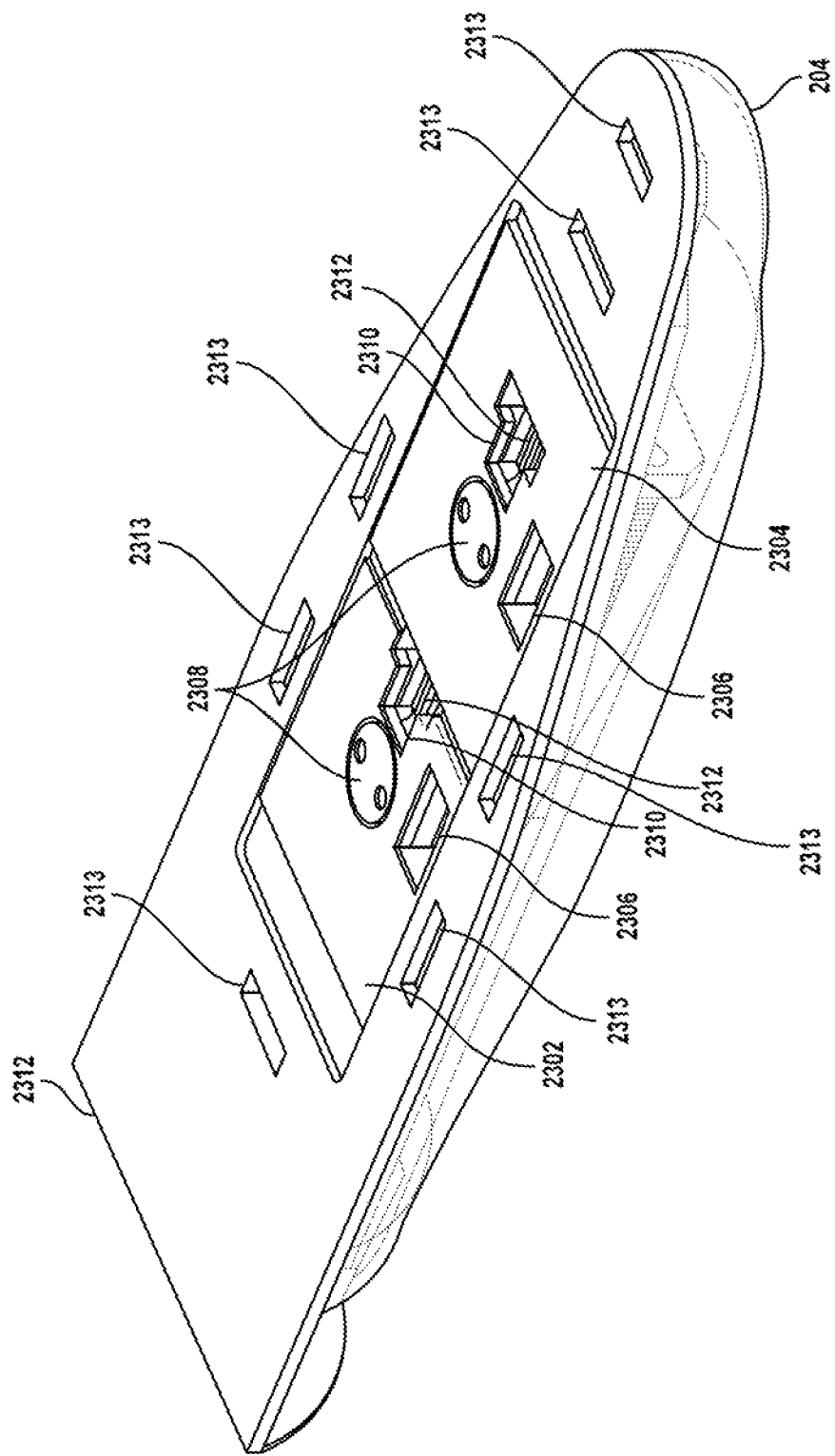

FIGS. 22A and 22B illustrate alternate views of the embodiment sled base shown in FIG. 21. FIG. 22A shows an oblique view of the sled member with a top covering 2312 with sockets 2313 for connecting a modular plate. FIG. 22B shows a bottom view of the sled member component of FIG. 21. As in FIG. 21, the sled member 204 has a first linkage 2302 and a second linkage 2304 that can translate. The first linkage 2302 and second linkage 2304 may have openings 2306 to provide access to a lead screw 2314 and openings 2310 to provide access to axial linkages 2312. The axle 2316 may also have bevel gears 2318 to drive rotating linkages 2308.

Figure 23:
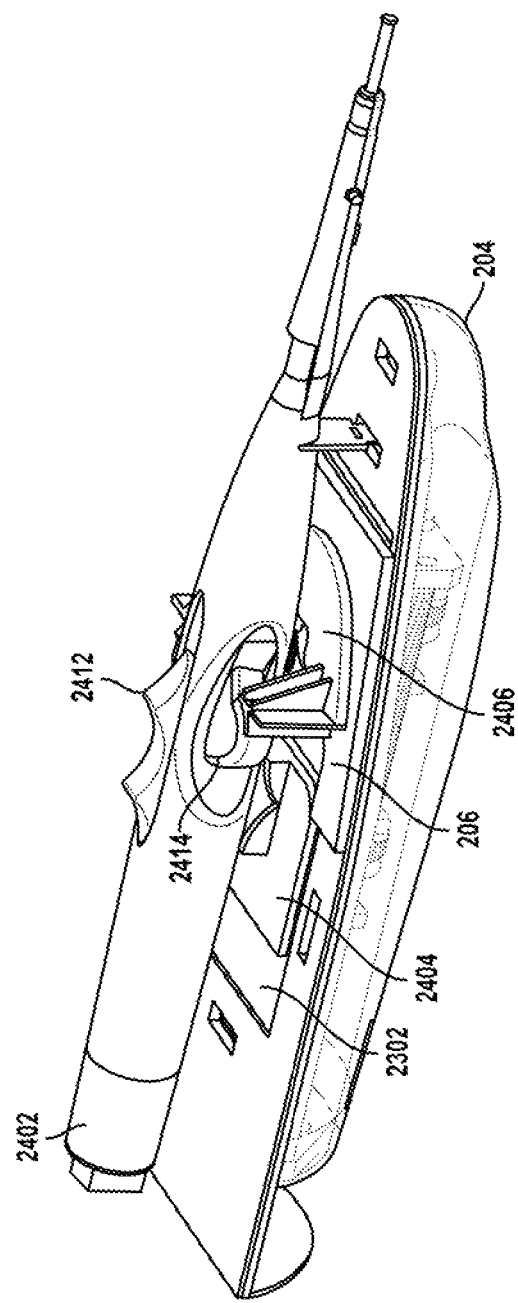
FIG. 23 is an oblique view of a catheter coupled with an embodiment sled member capable of controlling actuators in three different axes with multiple faces.

FIG. 23 illustrates an embodiment sled member 204 with a catheter 2402 installed that features a translating actuator 2412 and a rotating actuator 2414. The catheter 2402 may be coupled with a modular plate 206 to the sled member 204. The first linkage 2302 has been shifted back (i.e., to the left in FIG. 23) to adjust for the modular plate 206. The modular plate 206 may include a rotating actuator interface 2406 couple with the rotating linkage of the second plate (not shown). The modular plate 206 may also include a translating actuator interface 2404 that accesses the lead screw through the first face 2302.

Figure 24:
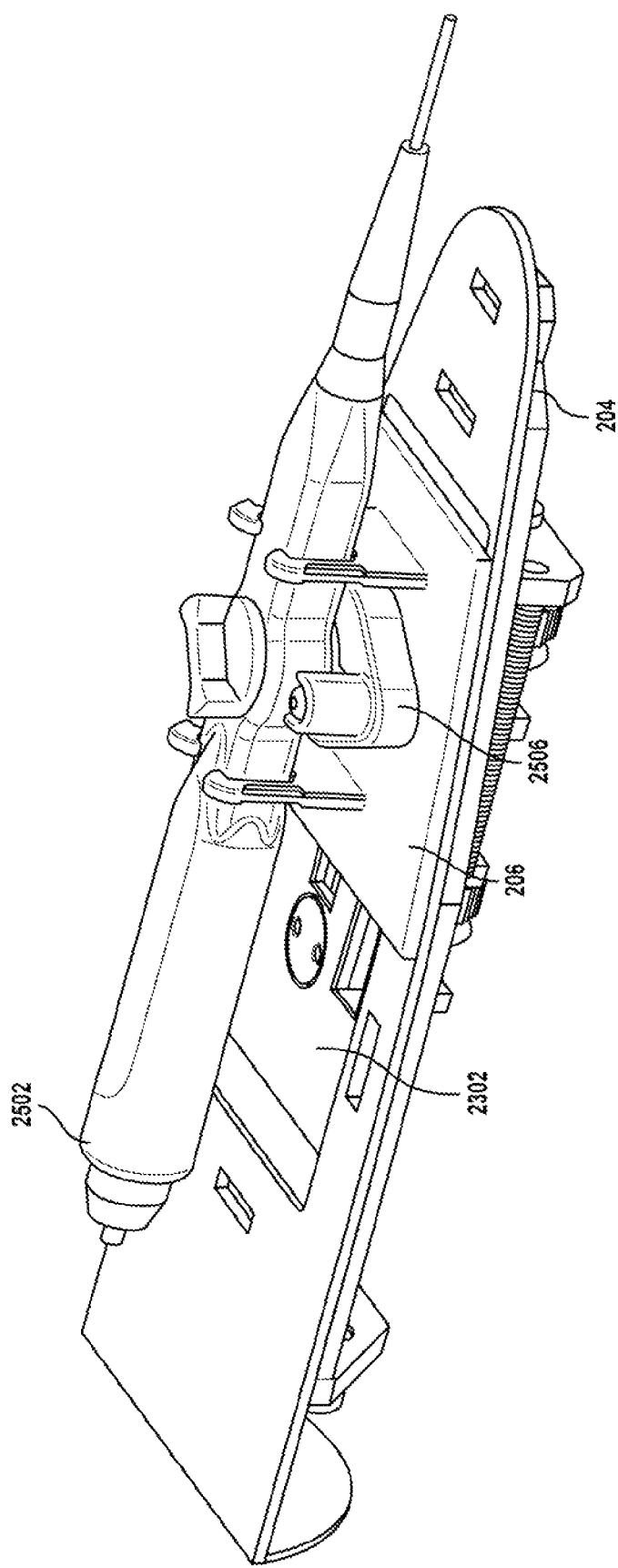
FIG. 24 is an oblique view of an alternate catheter coupled with an embodiment sled member capable of controlling actuators in three different axes with multiple faces.

FIG. 24 illustrates an alternate embodiment with a catheter 2502 with a single actuator. The first linkage 2302 may not need to be shifted if the single actuator can be controlled via an actuator interface 2506 on the modular plate 206 that couples with the second linkage on the sled member 204. Since the linkages of the first actuator interface 2302 are not needed to control the catheter 2502, the first linkage 2302 may be in any position.

Figure 25:
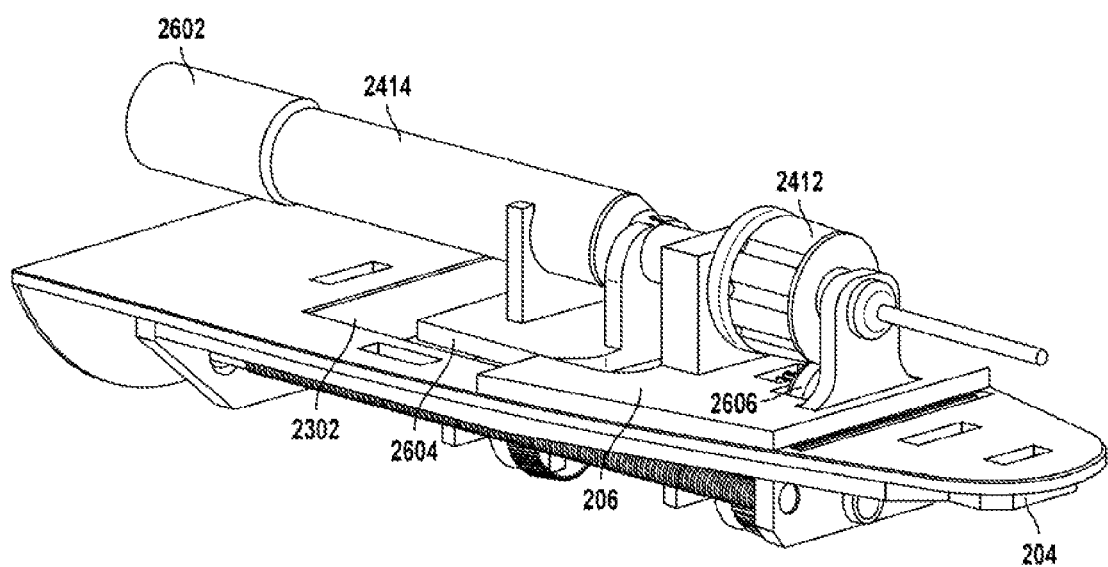
FIG. 25 is an oblique view of an alternate catheter coupled with an embodiment sled member capable of controlling actuators in three different axes with multiple faces.

FIG. 25 illustrates an alternate embodiment sled member with a different catheter 2602 installed featuring a translating actuator 2414 and an axial actuator 2412. The catheter may be coupled with a modular plate 206 with an axial actuator interface 2606 and a translating actuator interface 2604. The translating actuator interface 2604 may access the lead screw through the first linkage 2302. The axial actuator interface 2606 may access an axial linkage through the second linkage of the sled member 204.

Figure 26:
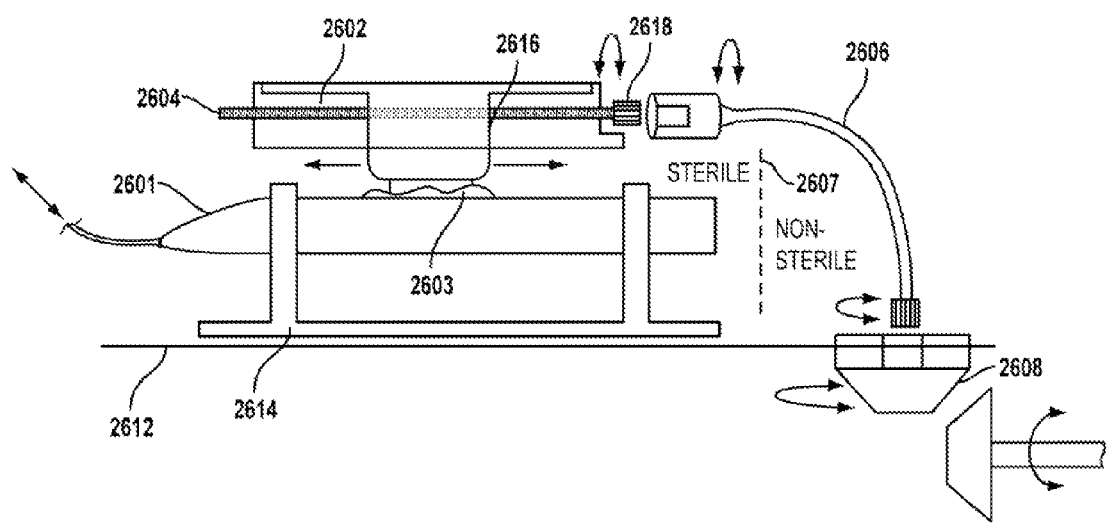
FIG. 26 is a cross sectional view of a catheter coupled with an embodiment clam shell sled member and modular plate.

In the various embodiments, the catheter contacting components of the sled members may be sterile components, either sterilizable or disposable, to avoid introducing contaminants into the body of a patient. In the various embodiments, sterility may be maintained using a variety of approaches individually or in combination, including barriers, multi-stage interfaces, distance/separation, etc. For example, a cross sectional view in FIG. 26 illustrates an embodiment clam shell sled member mated with a catheter/catheter handle 2601. Sterility may be maintained between sides of a sterility boundary 2607 by using a sterile intermediate flexible shaft 2606 as part of a two stage interface to actuate the slider 2603 of the catheter. The sterility boundary 2607 shown in FIG. 26 is for illustration purposes only and other and more sterility boundaries may be established anywhere sterility may be used, such as to isolate catheter components from drive mechanism components. A two stage interface may be an interface in which a first stage engages with a drive mechanism and may not remain sterile, and a second stage engages with the actuator and remains sterile. The two stage interface illustrated in FIG. 26 may include the flexible shaft 2606 as a first stage and the lead screw 2618 and slider actuator interface 2616 as a second stage. The catheter 2601 may be attached to the bottom portion 2612 of the clam shell sled member by a modular plate 2614. The top portion 2602 of the clam shell sled member may include the slider actuator interface 2616 interfacing with the slider 2603 of the catheter 2601. The docking plate 2614, slider actuator interface 2616, top portion 2604 of the clam shell sled member, and lead screw 2618 may be sterile because they may interact with the catheter 2601, and the flex shaft 2606 may also be sterile. The sterile flex shaft 2606 may separate the lead screw 2618 from the rotating linkage 2608 which may not be sterile. The rotating linkage 2608 may rotate, rotating the flex shaft 2606 that may rotate the lead screw 2618 to move the slider actuator interface 2616. The separation of the lead screw 2618 from the rotating linkage 2608 may enable a user to open the clam shell and remove the catheter 2601 without breaking sterility.

In all of the various embodiments, a remote controller and/or a control system, such as the control system described above with reference to FIG. 2 may be coupled to the various drive motors in the sled member to enable a user to remotely control the each drive motor to drive the respective linkages in order to rotate or translate linkages and actuator in order to manipulate the controls on the catheter handle.

While preferred embodiments have been described, the invention is only limited by the scope of the claims.

Those skilled in the art will recognize that the methods and systems of the present invention have many applications, may be implemented in many manners and, as such, is not to be limited by the preceding exemplary embodiments and examples. Additionally, the functionality of the components of the preceding embodiments may be implemented in different manners. Further, it is to be understood that the steps in the embodiments may be performed in any suitable order, combined into fewer steps or divided into more steps. Thus, the scope of the present invention covers conventionally known and future developed variations and modifications to the system components described herein, as would be understood by those skilled in the art.

What is claimed is:

1. A catheter positioning system for remotely controlling within a body of a patient a catheter having a proximal portion and a distal portion, the system comprising:
    a sled member configured to couple to a modular plate, the modular plate for interfacing with the catheter on the proximal portion thereof, the sled member comprising:
        a drive motor; and
        at least three drive linkages configured to be driven by the drive motor and to interface with an actuator on the modular plate, the actuator configured to actuate the catheter,
        wherein the at least three drive linkages are configured to provide actuation of actuator interfaces on the modular plate about two different axes,
        wherein the at least three drive linkages comprise:
            a translating linkage configured to drive translational movement;
            a rotating linkage configured to drive rotation about a first axis; and
            an axial linkage configured to drive rotation about a second axis.

2. The catheter positioning system of claim 1, wherein the at least three drive linkages are configured to provide actuation about the two different axes by being coupled together via bevel gears.

3. The catheter positioning system of claim 1, wherein the sled member comprises a clam shell sled having a top portion and a bottom portion configured to close around a handle of the catheter.

4. The catheter positioning system of claim 3, wherein the top portion and the bottom portion each comprise at least one linkage.

5. The catheter positioning system of claim 4, wherein the bottom portion is coupled with the modular plate and the top portion is coupled with a second modular plate.

6. The catheter positioning system of claim 4, wherein the bottom portion is coupled with the modular plate and the at least one linkage of the top portion is coupled with an actuator configured to actuate a control on a top surface of the handle of the catheter.

7. The catheter positioning system of claim 1, wherein the sled member comprises multiple actuator interfaces configured to actuate about a same axis.

8. The catheter positioning system of claim 7, wherein at least one of the multiple actuator interfaces is moveable on the sled member to accommodate different types of modular plates.

9. The catheter positioning system of claim 1, wherein the at least three drive linkages are configured to couple to the actuator interfaces on the modular plate by a multi-stage interface.

10. The catheter positioning system of claim 9, wherein the multi-stage interface is a two-stage interface configured to enable the catheter to be removed from the modular plate while maintaining sterility of the catheter.

11. The sled member of claim 10, wherein a first stage of the multi-stage interface is on a first side of a sterility boundary and a second stage of the two-stage interface is on a second side of the sterility boundary.

12. A sled member for interfacing with a catheter in a catheter positioning system for remotely controlling the catheter within a body of a patient, the sled member comprising:
    a clam shell having a top portion and a bottom portion configured to enclose a handle of the catheter;
    a drive motor; and
    at least three drive linkages coupled to the drive motor and configured to interface with an actuator on a first modular plate for coupling the catheter to the sled member,
    wherein the top portion and the bottom portion of the clam shell are configured to enclose the drive motor and the at least three drive linkages,
    wherein the at least three drive linkages comprise:
        a translating linkage configured to drive translational movement;
        a rotating linkage configured to drive rotation about a first axis; and
        an axial linkage configured to drive rotation about a second axis.

13. The sled member of claim 12, further comprising at least two actuator interfaces on a modular plate, wherein at least two of the at least three drive linkages are configured to provide actuation of the at least two actuator interfaces about at least two different axes.

14. The sled member of claim 12, further comprising bevel gears coupled to at least two of the at least three drive linkages and configured to provide actuation about two different axes by being coupled together via the bevel gears.

15. The sled member of claim 12, wherein the at least three drive linkages are enclosed in the bottom portion.

16. The sled member of claim 12, wherein the bottom portion is configured to interface with the first modular plate that is configured to interface with a first actuator on the handle of the catheter and the top portion is configured to interface with a second modular plate that is configured to interface with a second actuator on the handle.

17. The sled member of claim 12, wherein at least one of the at least three drive linkages is moveable on the sled member to accommodate different types of modular plates.

18. The sled member of claim 12, wherein at least two of the at least three drive linkages are configured to couple to actuator interfaces on a modular plate by a multi-stage interface that is configured to enable the catheter to be removed from the modular plate while maintaining sterility of the catheter.

19. A sled member for interfacing with a catheter in a catheter positioning system for remotely controlling the catheter within a body of a patient, the sled member comprising:
  a drive motor; and
  at least three drive linkages coupled to the drive motor and to each other in a configuration that provides actuation of catheter actuators on a modular plate,
  wherein the at least three drive linkages comprise:
    a translating linkage configured to drive translational movement;
    a rotating linkage configured to drive rotation about a first axis; and
    an axial linkage configured to drive rotation about a second axis.

* * * * *